United States Patent
Smitt et al.

(10) Patent No.: US 7,528,374 B2
(45) Date of Patent: May 5, 2009

(54) SENSING APPARATUS HAVING OPTICAL ASSEMBLY THAT COLLIMATES EMITTED LIGHT FOR DETECTION

(75) Inventors: Asbjorn Smitt, London (GB); Jason Lee, Daejeon (KR); Sung Woon Lee, Daejeon (KR); Sigird Smitt-Jeppesen, Reston, VA (US)

(73) Assignee: VIDAR Systems Corporation, Herndon, VA (US)

( * ) Notice: Subject to any disclaimer, the term of this patent is extended or adjusted under 35 U.S.C. 154(b) by 309 days.

(21) Appl. No.: 11/366,540

(22) Filed: Mar. 3, 2006

(65) Prior Publication Data

US 2007/0205365 A1 Sep. 6, 2007

(51) Int. Cl.
*G01J 5/02* (2006.01)
(52) U.S. Cl. .............................. 250/339.12; 250/458.1; 422/82.05
(58) Field of Classification Search ............ 250/339.12, 250/458.1, 403; 422/82.05
See application file for complete search history.

(56) References Cited

U.S. PATENT DOCUMENTS

| | | | |
|---|---|---|---|
| 5,863,504 A | 1/1999 | Heffelfinger et al. |
| 5,885,531 A | 3/1999 | Heffelfinger et al. |
| 6,024,920 A | 2/2000 | Cunanan |
| 6,185,030 B1 | 2/2001 | Overbeck |
| 6,201,639 B1 | 3/2001 | Overbeck |
| 6,215,894 B1 | 4/2001 | Zeleny et al. |
| 6,232,608 B1 | 5/2001 | Giebeler et al. |
| 6,236,456 B1 | 5/2001 | Giebeler et al. |
| 6,262,838 B1 | 7/2001 | Montagu |
| 6,313,471 B1 | 11/2001 | Giebeler et al. |
| 6,316,774 B1 | 11/2001 | Giebeler et al. |
| 6,335,824 B1 | 1/2002 | Overbeck |
| 6,345,115 B1 | 2/2002 | Ramm et al. |
| 6,352,672 B1 | 3/2002 | Mabile et al. |
| 6,362,004 B1 | 3/2002 | Noblett |
| 6,371,370 B2 | 4/2002 | Sadler et al. |
| 6,381,058 B2 | 4/2002 | Ramm et al. |
| 6,407,858 B1 | 6/2002 | Montagu |

(Continued)

FOREIGN PATENT DOCUMENTS

JP 2000 131237 5/2000

(Continued)

OTHER PUBLICATIONS

Pickett, Siobhan C., Understanding and Evaluating Fluorescent Microarray Imaging Instruments, *IVD Technology*, A Canon Communications LLC Publication, vol. 9, No. 4, May 2003.

*Primary Examiner*—David P Porta
*Assistant Examiner*—Djura Malevic
(74) *Attorney, Agent, or Firm*—Finnegan, Henderson, Farabow, Garrett & Dunner, LLP

(57) ABSTRACT

An apparatus for optical sensing of samples includes an optical source, an optical assembly, a sample holder, an objective lens, and a detector. The objective lens collimates light emitted by the sample. Preferably, the optical assembly rotates about an axis, allowing the sensing apparatus to sense results from plural locations on a sample without moving the sample. Moving the sample in a linear direction while rotating the optical assembly allows sensing of an entire sample. Preferably, light from the optical source enters the optical assembly along the axis of rotation. Sensing methods consistent with the invention are also described.

17 Claims, 19 Drawing Sheets

U.S. PATENT DOCUMENTS

| | | |
|---|---|---|
| 6,408,308 B1 | 6/2002 | Maslyn et al. |
| 6,441,973 B1 | 8/2002 | Ramm et al. |
| 6,448,089 B1 | 9/2002 | Vuong |
| 6,466,690 B2 | 10/2002 | Bacus et al. |
| 6,471,916 B1 | 10/2002 | Noblett |
| 6,496,309 B1 | 12/2002 | Bliton et al. |
| 6,498,690 B2 | 12/2002 | Ramm et al. |
| 6,545,758 B1 | 4/2003 | Sandstrom |
| 6,555,802 B2 | 4/2003 | Osipchuk et al. |
| 6,567,163 B1 | 5/2003 | Sandstrom |
| 6,583,424 B2 | 6/2003 | Staton et al. |
| 6,586,257 B1 | 7/2003 | Vuong |
| 6,617,590 B2 | 9/2003 | Nishioka et al. |
| 6,628,385 B1 | 9/2003 | Osipchuk et al. |
| 6,633,659 B1 | 10/2003 | Zhou |
| 6,638,483 B2 | 10/2003 | Vuong |
| 6,646,271 B2 | 11/2003 | Yokokawa et al. |
| 6,658,429 B2 | 12/2003 | Dorsett, Jr. |
| 6,731,781 B1 | 5/2004 | Shams et al. |
| 6,740,871 B1 | 5/2004 | Staton et al. |
| 6,754,414 B2 | 6/2004 | Naghieh et al. |
| 6,794,658 B2 | 9/2004 | MacAulay et al. |
| 6,804,679 B2 | 10/2004 | Jevons et al. |
| 6,806,954 B2 | 10/2004 | Sandstrom |
| 6,814,933 B2 | 11/2004 | Vuong |
| 6,831,994 B2 | 12/2004 | Bridgham et al. |
| 6,833,916 B2 * | 12/2004 | Osipchuk et al. ............ 356/318 |
| 6,839,454 B1 | 1/2005 | Park |
| 6,927,389 B2 | 8/2005 | Curry et al. |
| 6,947,142 B2 | 9/2005 | Chen et al. |
| 6,950,756 B2 | 9/2005 | Kincaid |
| 6,954,699 B2 | 10/2005 | Jevons et al. |
| 6,956,203 B2 | 10/2005 | Staton et al. |
| 6,995,902 B2 | 2/2006 | Wang et al. |
| 7,013,220 B2 | 3/2006 | Dorsel et al. |
| 7,031,507 B2 | 4/2006 | Bacus et al. |
| 7,031,844 B2 | 4/2006 | Bozinov et al. |
| 7,034,941 B2 | 4/2006 | Chen et al. |
| 7,042,565 B2 | 5/2006 | Wang et al. |
| 7,050,208 B2 | 5/2006 | Overbeck |
| 7,062,091 B2 | 6/2006 | Brown et al. |
| 7,062,092 B2 | 6/2006 | Kaushikkar et al. |
| 7,070,740 B1 | 7/2006 | Matson et al. |
| 7,072,500 B2 | 7/2006 | Cerrina et al. |
| 7,079,673 B2 | 7/2006 | Foran et al. |
| 7,081,954 B2 | 7/2006 | Sandstrom |
| 7,084,661 B2 | 8/2006 | Thompson et al. |
| 7,089,123 B2 | 8/2006 | Corson et al. |
| 7,095,032 B2 | 8/2006 | Montagu et al. |
| 7,099,502 B2 | 8/2006 | Shams et al. |
| 7,126,688 B2 | 10/2006 | Rassman et al. |
| 7,135,667 B2 | 11/2006 | Oldham et al. |
| 7,154,598 B2 | 12/2006 | Montagu et al. |
| 7,171,030 B2 | 1/2007 | Foran et al. |
| 7,175,811 B2 | 2/2007 | Bach et al. |
| 2002/0005493 A1 | 1/2002 | Reese et al. |
| 2002/0062202 A1 | 5/2002 | Arai |
| 2002/0147512 A1 | 10/2002 | Bernhart et al. |
| 2002/0154396 A1 | 10/2002 | Overbeck |
| 2003/0039383 A1 | 2/2003 | Naghieh et al. |
| 2003/0057379 A1 | 3/2003 | Montagu |
| 2003/0124589 A1 | 7/2003 | Piper |
| 2003/0161514 A1 | 8/2003 | Curry |
| 2003/0215882 A1 | 11/2003 | Grossman et al. |
| 2003/0219196 A1 | 11/2003 | Weng et al. |
| 2004/0012676 A1 | 1/2004 | Weiner et al. |
| 2004/0072274 A1 | 4/2004 | Lebrun |
| 2004/0081985 A1 | 4/2004 | Ciccolella et al. |
| 2004/0110172 A1 | 6/2004 | Olson et al. |
| 2004/0160607 A1 | 8/2004 | Lin et al. |
| 2004/0181342 A1 | 9/2004 | Zhou |
| 2004/0234114 A1 | 11/2004 | Amakawa et al. |
| 2004/0253614 A1 | 12/2004 | Yonekawa et al. |
| 2005/0006595 A1 | 1/2005 | Goodwin et al. |
| 2005/0009055 A1 | 1/2005 | Ciccolella et al. |
| 2005/0112773 A1 | 5/2005 | Vuong |
| 2005/0118640 A1 | 6/2005 | Kureshy et al. |
| 2005/0134858 A1 | 6/2005 | Wu et al. |
| 2005/0221351 A1 | 10/2005 | Ryu |
| 2005/0239113 A1 | 10/2005 | Ryu et al. |
| 2005/0239114 A1 | 10/2005 | Ryu et al. |
| 2005/0239115 A1 | 10/2005 | Ryu et al. |
| 2005/0247887 A1 | 11/2005 | Trulson et al. |
| 2005/0260741 A1 | 11/2005 | Albertson et al. |
| 2005/0281708 A1 | 12/2005 | Trulson et al. |
| 2006/0001955 A1 | 1/2006 | Kinney et al. |
| 2006/0078948 A1 | 4/2006 | Matsui et al. |
| 2006/0094027 A1 | 5/2006 | Warren et al. |
| 2006/0105354 A1 | 5/2006 | Remacle et al. |
| 2006/0166355 A1 | 7/2006 | Gutekunst |
| 2006/0194308 A1 | 8/2006 | Gutekunst et al. |
| 2006/0217913 A1 | 9/2006 | Kaushikkar et al. |
| 2006/0238846 A1 | 10/2006 | Alexander et al. |
| 2006/0253035 A1 | 11/2006 | Stern |
| 2006/0269450 A1 | 11/2006 | Kim |
| 2006/0274922 A1 | 12/2006 | Ragsdale |
| 2007/0026532 A1 | 2/2007 | Ikami |
| 2007/0031856 A1 | 2/2007 | Hong |
| 2007/0037146 A1 | 2/2007 | Hong |

FOREIGN PATENT DOCUMENTS

| | | |
|---|---|---|
| JP | 2002-181708 | 6/2002 |
| JP | 2003 139776 | 5/2003 |
| JP | 2004 020441 | 1/2004 |
| JP | 2004 184379 | 7/2004 |
| WO | WO 2006/110135 | 10/2006 |
| WO | WO 2006/128321 | 12/2006 |
| WO | WO 2006/128322 | 12/2006 |
| WO | WO 2006/128325 | 12/2006 |

* cited by examiner

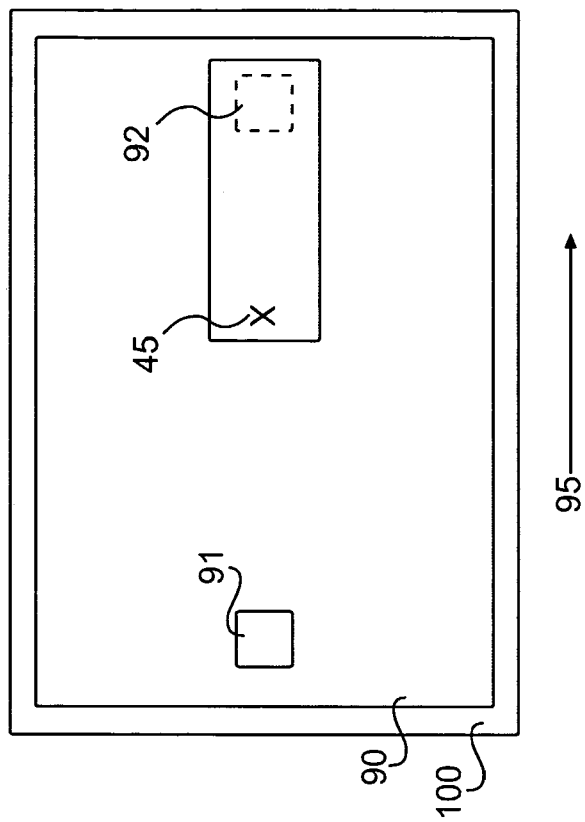
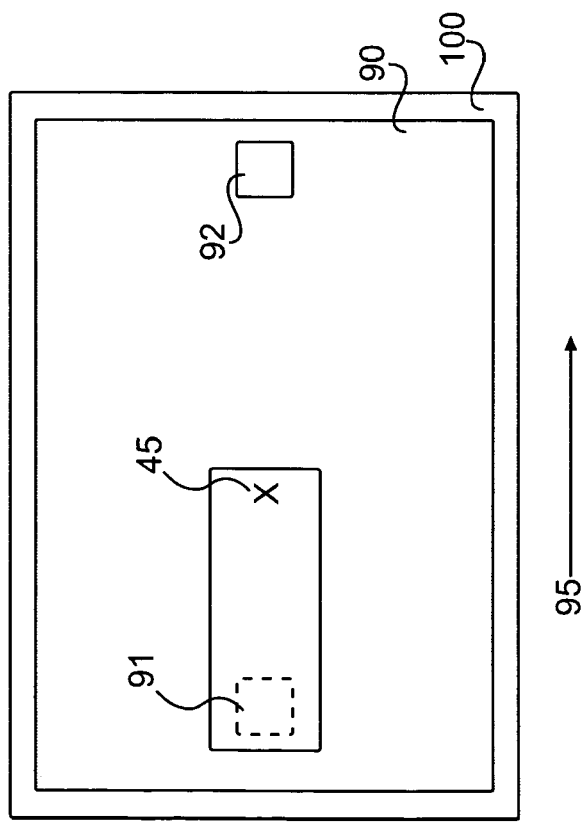

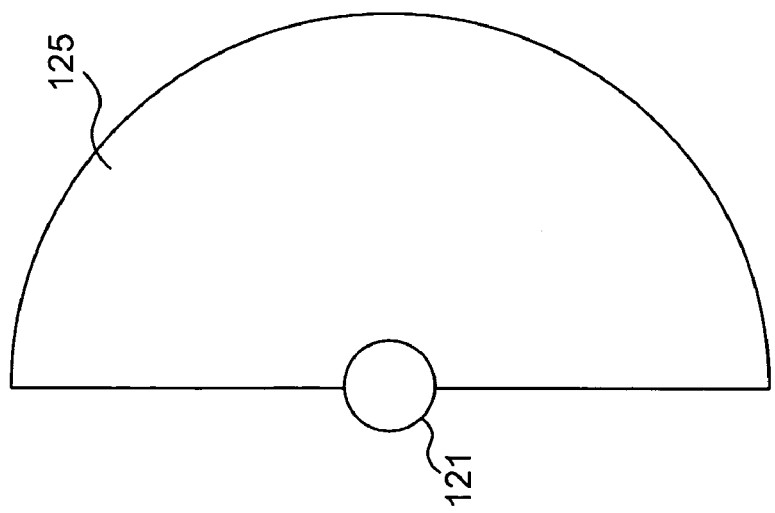
*FIG. 7B*
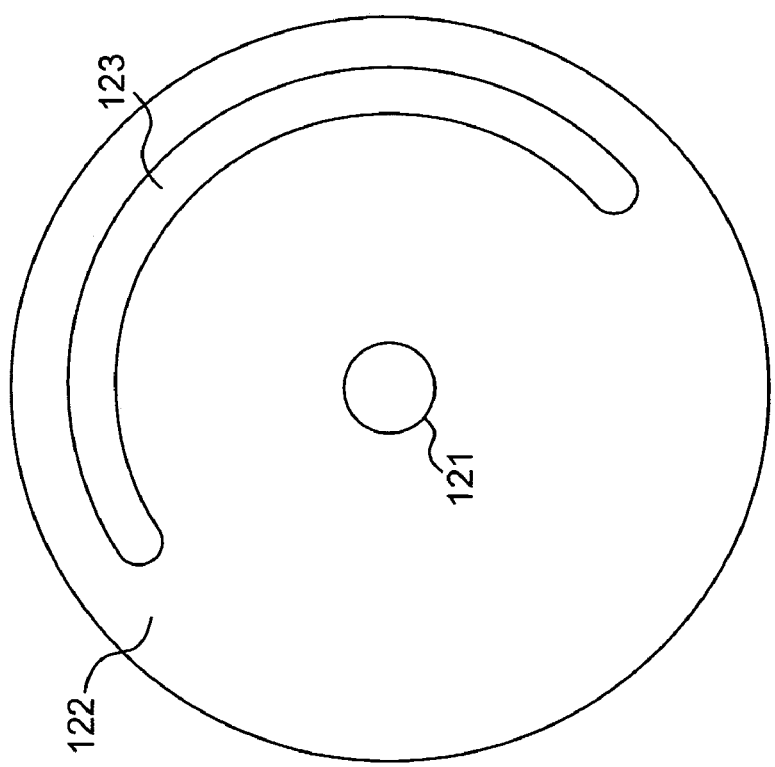
*FIG. 7A*
*FIG. 7*

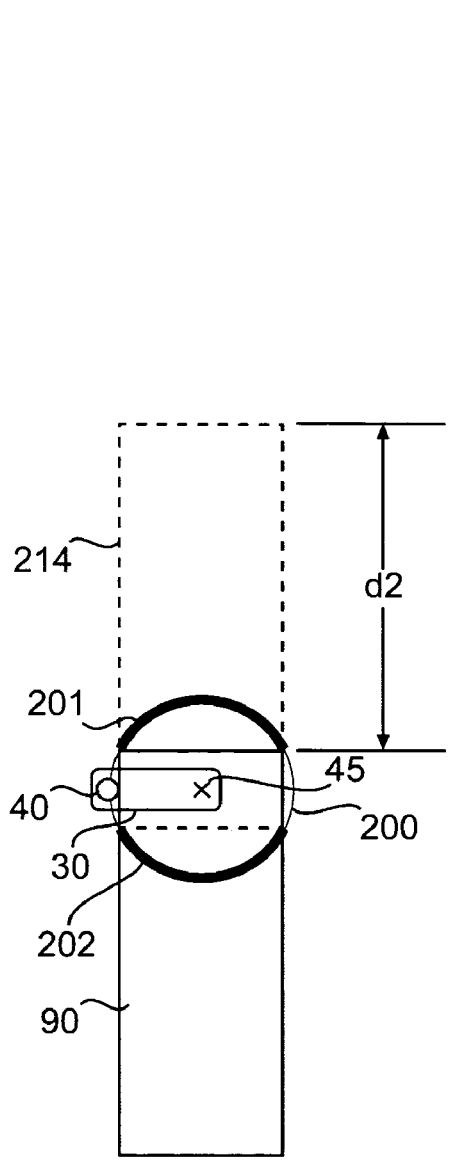
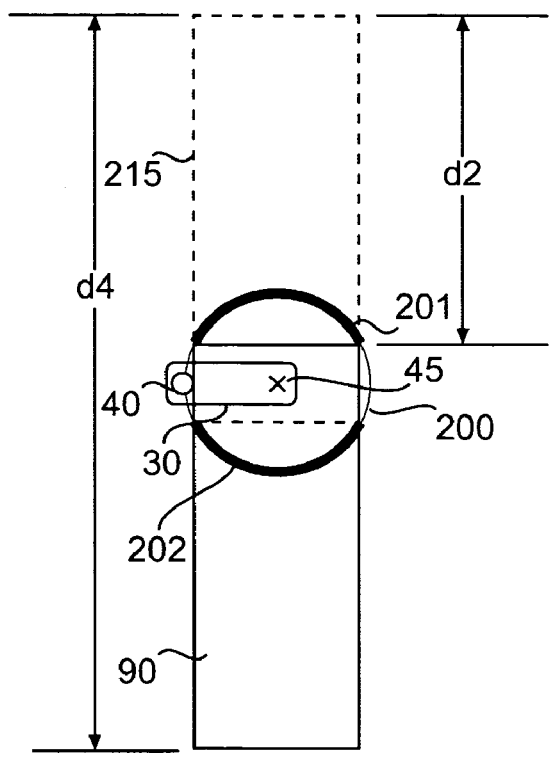
FIG. 14B
FIG. 14A

SENSING APPARATUS HAVING OPTICAL ASSEMBLY THAT COLLIMATES EMITTED LIGHT FOR DETECTION

BACKGROUND

1. Field

The present invention relates to the field of sample sensing.

2. Description of Related Art

Conventional sensing apparatuses use one or more optical sources to read samples. Biochip scanners, for example, use laser light to irradiate a chemical or biological sample, which, depending on material in the sample, responds by fluorescing. By detecting the light emitted by the sample, conventional apparatuses can identify specific materials in the sample, as well as the amount of those materials present. In one application, sensing apparatuses may be used, for example, to capture results from multiple reactions in real time by rapidly scanning the sample surface.

The samples may include, for example, a biochip. As appreciated by those of skill in the art, a biochip is a collection of test sites arranged on a solid substrate. These biochips allow scientists to monitor multiple chemical or biochemical reactions simultaneously, and have applications in genetics, toxicology, biochemical, protein, and other research areas related to chemistry and biochemistry. A biochip may contain thousands of individual test sites, each representing the outcome of an individual reaction.

Typically, conventional sensing apparatuses irradiate and monitor only one test site at time until each test site on the sample has been exposed. Conventional biochip scanners, for example, move either the sample or the body of the sensing apparatus in a linear or grid fashion, directing light to each individual test site on the sample. In this manner, the sensing apparatus scans each individual test site to determine whether it contains the material or materials to be sensed.

Conventional systems typically focus light emitted from the fluorescing sample onto a detector, such as a charge-coupled device or photomultiplier tube. A collection lens is typically placed so that its focal point coincides, or nearly coincides with a light-sensing surface of the detector. Such systems may also include a pin-hole lens to increase the signal-to-noise ration of the sensing system. The collection lens and/or pin-hole lens, however, increases manufacturing and assembly costs of the sensing system and adds to sensing system bulk and weight of the system.

Sensing and mapping materials on samples with multiple test sites in real-time requires sensing apparatuses capable of quickly directing and receiving light from distinct locations on the sample. Quickly collecting data from samples containing thousands of individual experimentation sites, like biochips, speeds research and saves laboratory resources. To effectively capture experimental results, therefore, it is desirable to provide sensing apparatuses and methods that hasten sample sensing.

Moreover, sensing apparatuses and methods capable of detecting materials on samples containing multiple test sites arranged in a non-rectilinear pattern create flexibility for users. Samples containing multiple test sites arranged in spirals, circles, or arcs, for example, provide enhanced sensing opportunities. While arranging test sites in a pattern other than a grid allows for a higher density of test sites on the sample, conventional sensing apparatuses are not configured to read samples laid out in this manner.

Additionally, it is desirable to create apparatuses and sensing methods that sense samples without moving the samples in rectilinear fashion, as done in conventional sensing apparatuses. Such apparatuses and methods can scan samples containing non-rectangular test sites.

SUMMARY OF THE INVENTION

A sensing apparatus is provided, which comprises a sample holder configured to receive a sample, an optical source, an optical assembly, an objective lens module, and a detector. The optical assembly is spaced from the sample holder, and is configured to receive excitation light outputted by the optical source and to direct the excitation light to a first location on the sample when the optical assembly is in a first position. The optical assembly also directs the excitation light to a second location on the sample when the optical assembly is rotated to a second position. The objective lens module collimates light emitted from the first and second locations on the sample, which is fluoresced in response to the first light. The detector is configured to receive and detect this emitted light.

It is to be understood that both the foregoing general description and the following detailed description are exemplary and explanatory only and are not restrictive of the invention, as claimed.

The accompanying drawings, which are incorporated in and constitute a part of this specification, illustrate several embodiments consistent with the invention and together with the description, serve to explain the principles of the invention.

BRIEF DESCRIPTION OF THE DRAWINGS

FIGS. 4A and 4B are schematic diagrams of an optical assembly consistent with an embodiment of the invention.

FIGS. 7A and 7B illustrate light-interruption plates for use in sensing apparatuses consistent with embodiments of the invention;

FIGS. 11, 12, 13A, 13B, 14A, 14B, and 15 are schematic diagrams showing operational modes for sensing apparatuses consistent with embodiments of the invention.

DETAILED DESCRIPTION OF THE PREFERRED EMBODIMENTS

Reference will now be made in detail to exemplary embodiments consistent with the invention, illustrated in the accompanying drawings. Wherever possible, the same reference numbers will be used throughout the drawings to refer to the same or like parts.

Figure 1:
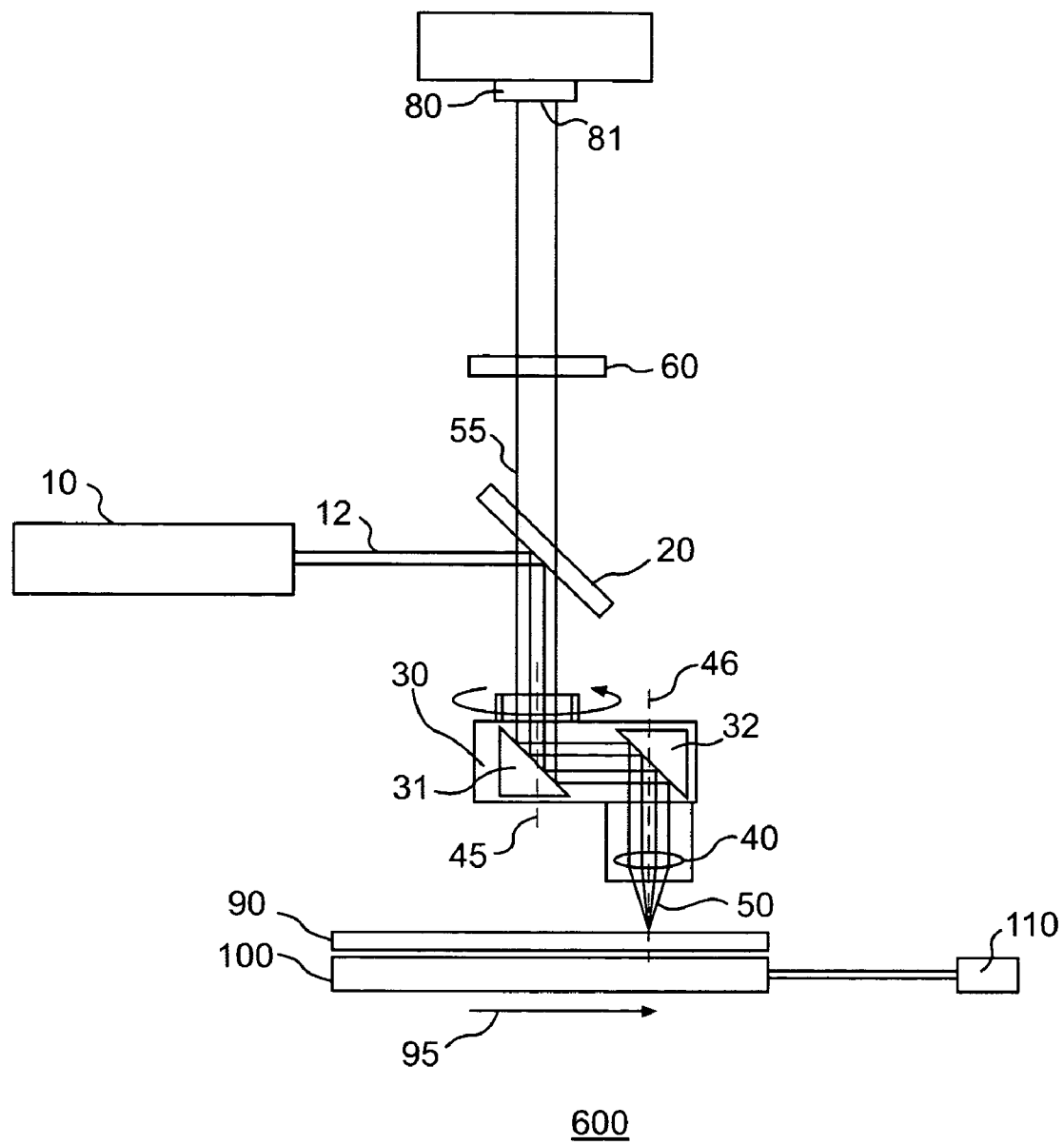
FIG. 1 is a schematic diagram of a first sensing apparatus consistent with an embodiment of the invention.

FIG. 1 illustrates a sensing apparatus 600 consistent with the present invention. Sensing apparatus 600 comprises an optical source 10, an optical assembly 30, an objective lens module 40, a detector 80, and a sample holder 100. A sample 90, including a biochip, for example, is loaded into sample holder 100. As further shown in FIG. 1, sensing apparatus 600 further includes a first optical filter 20 and a second optical filter 60, used as an emission filter. Components of sensing apparatus 600 will next be described in greater detail.

Optical source 10 outputs excitation light 12 to optical filter 20. Optical source 10 preferably comprises a laser, in which case excitation light 12 constitutes a laser beam having a single wavelength and phase. The preferable wavelength of excitation light 12 depends on sample 90. For example, green laser light is typically used to sense materials including Cy3 dye, while red laser light is used to sense materials including Cy5 dye. Both of these dyes are known and can be provided in conventional sensing systems to scan samples, such as biochips. Lasers suitable for use in a sensing apparatus include, for example, the model LVI-VA-532-30 laser, commercially available from LVI Technology Co., Ltd. (typically used with Cy3 dye) or the LM-6535GR laser, commercially available from Lanics Co., Ltd (typically used with Cy5 dye).

When excitation light 12, generated by optical source 10, reaches optical filter 20, optical filter 20 reflects excitation light 12 toward optical module 30. In particular, when excitation light 12 includes a particular wavelength or band of wavelengths, optical filter 20 can be selected to reflect substantially all of excitation light 12 toward optical module 30. Thus, optical filter 20 is preferably a dichroic reflector, especially if excitation light 12 constitutes a laser beam or similar single-wavelength optical source.

Optical assembly 30, which is spaced from sample holder 100, receives excitation light 12 reflected from filter 20 and directs excitation light 12 to sample 90.

In preferred embodiments, optical assembly 30 includes one or more mirrors to direct excitation light 12 to sample 90. In FIG. 1, for example, optical assembly 30 comprises a first mirror 31 and a second mirror 32. First mirror 31 is located on axis 45, while second mirror 32 is located a distance apart from mirror 31 along axis 46. Optical module 30 receives excitation light 12 along axis 45, mirror 31 then reflects excitation light 12 toward mirror 32, which in turn, directs excitation light 12 to sample 90 along axis 46.

Preferably, mirror 31 is arranged at substantially 45° relative to axis 45. In this preferred arrangement, first mirror 31 reflects excitation light 12 in a direction substantially perpendicular to axis 45. Second mirror 32, located a distance away from first mirror 32, reflects excitation light 12 so that it travels in a direction substantially parallel to axis 45. Mirror 32 is arranged at substantially 45° relative to axis 46 to reflect excitation light 12 to objective lens assembly 40. In the configuration illustrated in FIG. 1, axes 45, 46 are substantially perpendicular to the surface of sample 90. If desired, however, axes 45, 46 may be oriented at different angles relative to the surface of sample 90, as well as each other.

Moreover, excitation light 12 need not enter optical assembly 30 along axis 45. Configurations in which light optical assembly 30 receives excitation light 12 along an axis other than axis 45 are consistent with the present invention. For example, mounting optical source 10 to optical assembly 30 would allow light to enter the optical module along an axis other than axis 45, such as, for example, axis 46. Such a configuration could eliminate the need for mirrors 31, 32.

Preferably, mirrors 31, 32 are of a type well known in the art, such as 02MFG00 mirrors, which are commercially available from Melles Griot, Inc.

Excitation light 12 next passes through objective lens assembly 40, which includes one or more objective lenses. Objective lens assembly 40 focuses excitation light 12, limiting the beam of light transmitted to sample 90 to a desired size, so that a desired portion of sample 90 may be exposed. Also, once focused, excitation light 12 has a greater intensity than the input to assembly 30. The resulting fluorescence of sample 90 may thus also increase, facilitating more accurate measurements.

After passing through objective lens assembly 40, excitation light 12 reaches a location on sample 90. Excitation light 12 causes the location on sample 90 to fluoresce and emit light 50. Specifically, sample 90 may emit photons of light as electrons of atoms contained in sample 90 are excited in response to excitation light 12 and then relax into a lower energy state.

The amount of emitted light 50 emitted by sample 90, if any, may depend on the result of an experiment performed on sample 90. Due to a biological or biochemical reaction, for example, sample 90 may contain a material that fluoresces in response to excitation light 12.

Optical assembly 30 receives emitted light 50 through objective lens module 40, which collimates and directs emitted light 50. Specifically, objective lens assembly 40 collimates emitted light 50 into beam 55 having a predetermined width. The photons of light making up beam 55 travel substantially parallel to one another as they move through sensing apparatus 600. Thus, collimating emitted light 50 into beam 55 substantially prevents the emitted photons from scattering before reaching detector 80.

To collimate emitted light 50, objective lens module 40 preferably comprises an aspherical lens, which focuses excitation light 12 onto a location on sample 90 and collimates emitted light 50 into a beam. Optical assembly 30 directs beam of emitted light 50 toward detector 80.

After being collimated by objective lens module 40, beam 55 reflects off of mirrors 32 and 31 in optical assembly 30. Beam 55 then exits optical assembly 30 and substantially passes through optical filter 20 and optical filter 60, before reaching detector 80.

Optical filter 20 does not reflect beam 55, which comprises emitted light 50 emitted by sample 90. Indeed, emitted light 50 substantially passes through optical filter 20 before reaching detector 80. Excitation light 12 and emitted light 50 have distinct wavelengths, allowing sensing apparatus 600 to separate them using optical filter 20, which, as mentioned above, typically includes a dichromc filter. Preferably, optical filter 20 is a known filter having a coating configured to reflect light at the wavelength of excitation light 12, but to permit other wavelengths to pass.

Beam 55 next passes through optical filter 60, which attenuates light of unwanted wavelengths from emitted light 50. Optical filter 60, typically a band-pass filter, allows only light having a desired wavelength to substantially pass through. Skilled artisans may also refer to a filter for this application as an emission filter. Optical filter 60 substantially attenuates any excitation light 12, generated by optical source 10, reflected off of sample 90 and mixed in with emitted light 50 after passing through optical filter 20. Optical filter 60 thus may ease signal processing by substantially attenuating any extraneous light—whether excitation light 12 or other light that happens to find its way into the collimated beam of emitted light 50. Optical filter 60 may include the 51007m optical filter, commercially available from Chroma Technology Corporation, or other known filters.

Detector 80 converts the light received, or a portion thereof, into corresponding electrical signals that it receives to create an appropriate electrical signal, which a user or computer can use, store, and/or analyze. Because objective lens module 40 collimates emitted light 50 into beam 55, most of the photons contained in emitted light 50 strike the light-sensing surface 81 of detector 80. If emitted light 50 was not formed into beam 55, however, a higher percentage of the photons emitted by sample 90 would scatter before striking light-sensing surface 81 of detector 80. If this were the case, the scattering of emitted photons would detract from the overall image quality produced by the sensing apparatus.

Instead of creating a substantially parallel beam of emitted light, conventional sensing systems typically focus emitted light prior to detection. Some systems employ a collection lens, which focuses the emitted light onto the light-sensing surface of the detector. Other systems use a pin-hole to eliminate unwanted light before it enters a detector, which increases the signal-to-noise ratio of the sensing system. A pin-hole lens has the advantage of being nearly loss-less, as it does not scatter photons contained in the emitted light, as may occur with a glass collection lens. Some systems use both a pin-hole lens and a collection lens. Sensing apparatus 600, however, contains neither a collection lens nor a pin-hole to focus emitted light 50 before it enters detector 80.

Detector 80 preferably comprises a Photomultiplier Tube (PMT) detector or other highly-sensitive detector. As a PMT amplifies each photon that it receives, such a detector can adequately sense the light emitted by sample 90. An exemplary photo multiplying tube consistent with this application is the H6779 tube, commercially available from Hamamtsu Photonics, K.K.

Including a sensitive detector, such as s PMT detector, in detector 80 allows sensing apparatus 600 to sense emitted light received from a very small portion of sample 90. Preferably, sensing apparatus 600 can sense light fluoresced by an area on the order of 1 micron. When optical source 10 comprises a laser, which objective lens module 40 focuses on sample 90, sensing apparatus 600 can illuminate such a small portion of sample 90.

Preferably, beam 55 substantially covers light-sensing surface 81 of detector 80. For example, where detector 80 comprises a PMT detector, it is advantageous for beam 55 to substantially cover a photocathode of the PMT detector. In this manner, most of the photons emitted by the location on sample 90 reach, and are detected by, detector 80.

Detectors containing Charge-Coupled Devices (CCDs) may, in some circumstances, not provide sufficient sensing capabilities for inclusion in detector 80. Detectors using CCDs include an array of small discrete sensing locations. Because the photons included in the substantially parallel beam of emitted light 50 will likely impinge on multiple sensing locations in this array, the CCD may not exhibit the sensitivity necessary to act as a part of detector 80.

Preferably, optical assembly 30, described above, is rotatable about axis 45, so that excitation light 12 can be directed to multiple locations on sample 90 without moving sample 90. Optical assembly 30 can be configured to rotate in a full circle, a semicircle, or an arc. Due to the rotation of optical module 30, second mirror 32 follows an arc about axis 45. The distance between mirrors 31 and 32 defines the radius of this arc. This arc may constitute a semi-circle or a full circle, and can be any appropriate length.

As illustrated in FIG. 4A, at a first position, optical assembly 30 directs excitation light 12 to a first location 91 on sample 90 and receives emitted light 50 from first location 91 on sample 90. When optical assembly 30 rotates to a second position, illustrated in FIG. 4B, it directs excitation light 12 to a second location 92 on sample 90 and receives emitted light 50 from second location 92 on sample 90. Thus, over time, as optical assembly 30 rotates, excitation light 12 is directed to plural locations on sample 90. Moreover, sample holder 100 moves in linear direction 95 relative to axis 45, allowing sensing apparatus 600 to direct excitation light 12 to all locations on sample 90.

As illustrated in FIG. 4A and FIG. 4B, first location 91 and second location 92 may be located substantially opposite one another on a circle defined by the rotation of optical assembly 30 about axis 45. When first location 91 and second location 92 are located in this manner, sensing apparatus 600 may sense emitted light 50 from each of locations 91, 92 during a single rotation of optical assembly 30. By sensing from plural locations on each rotation of optical assembly 30, the time required to sense emitted light from all desired locations on sample 90 decreases. While this configuration of sensing apparatus 600 is preferable, first location 91 and second location 92 may be located adjacent to one another on sample 90, or in any other desired configuration. Moreover, it may be possible to sense emitted light from more than two locations on sample 90 with each rotation of optical assembly 30. To differentiate emitted light 50 from emitted light 61, it may be necessary to adjust the shutter time of detector 80.

Figure 17A:
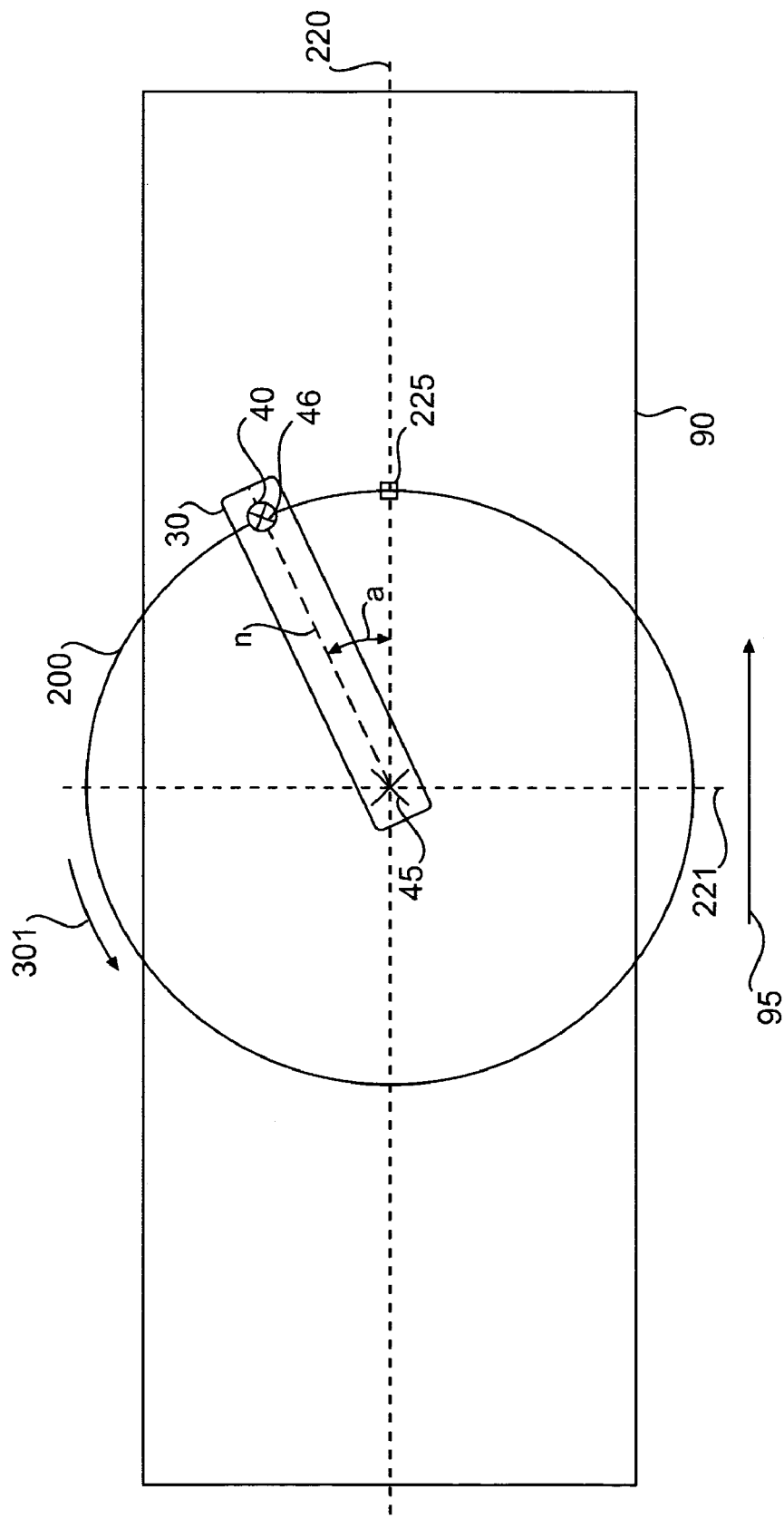
FIG. 17A-17C are schematic diagrams illustrating methods of creating images representing the light emitted by a sample, consistent with embodiments of the invention.

As illustrated in FIG. 17A, optical assembly 30 preferably rotates about axis 45, in a direction indicated by arrow 301, with a substantially constant angular speed. This constant angular speed allows sensing apparatus 600 to identify the plural locations on sample 90 from which it senses emitted light. The rotation of optical assembly 30 about axis 45 defines rotational sensing circle 200, with a radius v extending from axis 45 to axis 46.

Sample holder 100 holds sample 90 in place for sensing. As discussed above, the rotation of optical module 30 allows sensing apparatus 600 to direct excitation light 12 to multiple locations on sample 90 without moving sample 90. Thus, sample holder 100 may remain in one location.

Preferably, however, sample holder 100 moves along a substantially straight line (hereinafter "in a linear direction"). Moving sample 90 in a linear direction, when combined with the rotation of optical module 30, allows sensing apparatus 600 to direct excitation light 12 to all locations on sample 90 and to receive emitted light 50 from all locations on sample 90. In this manner, sensing apparatus 600 can create a two-dimensional image of the sample from the electrical signals gathered by detector 80. Thus, the sensing apparatus 600 can quickly scan samples, such as biochips having the "2-dimension & large" format. In addition, by moving sample 90 and optical assembly 30 in both linear and rotational directions relative to one another, sensing apparatus 600 decreases sensing time and enables continuous sample scanning. Persons of skill in the art will perceive other advantages of this configuration.

Linear stage module 110 moves sample holder 100 in a linear direction. Preferably, linear stage module 110 comprises a stepper motor configured to move sample 100 in a linear direction substantially perpendicular to axis 45 in a stepwise fashion. Linear stage module may include, for example, a stepper motor such as the model KH42JM2-901 stepper motor, commercially available from Japan Servo Co., Ltd. Moreover, sample holder 100 may remain stationary while the rest of sensing apparatus 600 moves in a linear direction in addition to the rotating motion discussed above.

Optionally, movement of sample holder 100 may comprise a non-linear motion and/or continuous motion. Non-linear motion may be desirable where sample 90 comprises non-rectangular test sites or test sites arranged in a manner other than a rectilinear grid. Where sample holder 100 moves in a non-linear manner, Sensing apparatus 600 would include another apparatus, such as a four-bar linkage, to move sample holder 100 instead of linear stage module 110.

Preferably, sample 90 includes a biochip. Sensing apparatus 600 can direct excitation light 12 and detect emitted light 50 from multiple locations on sample 90, making sensing apparatus 600 well-suited for use with biochips or other samples having multiple test sites.

Preferably, sensing apparatus 600 detects emitted light from multiple regions on sample 90, each region typically having a square shape with sides substantially equal to the distance that sample 90 travels during each a full rotation of optical assembly 30 around axis 45. Region 225, illustrated in FIG. 17A, is an example of such a region and is positioned where rotational sensing circle 200 meets reference line 220. Reference line 220 is a reference line, drawn with dashed lines, substantially parallel to direction 95 and passing through the middle of sample 90. As shown in FIG. 17A, reference line 221, a second reference line for purposes of this discussion, is substantially orthogonal to reference line 220 and also passes through the middle of sample 90. Reference lines 220, 221 are used for purposes of discussion, but may not necessarily be present on sample 90.

Preferably a computer, not shown, is coupled to detector 80 and captures multiple pixels, each of which typically represents light emitted by a particular region on sample 90. To "capture" each pixel, the computer reads an output from detector 80 and stores information—the pixel—representing the light detected by detector 80 for later use. The computer later uses these multiple captured pixels to create an image of the light emitted by sample 90. To create an accurate image, the computer determines the region on sample 90, such as region 225, to which each captured pixel corresponds and places the pixel in its proper place in the image. Preferably, the image has a uniform resolution in rectilinear coordinates.

The computer may use a timer and the constant angular speed at which optical assembly 30 rotates to correlate pixels captured from detector 80 with regions on sample 90 to create the desired image of light emitted by sample 90. The computer can create the desired image in multiple ways, such as varying the timing it uses to capture pixels from detector 80.

For example, in a first preferable method of creating an image of light emitted by sample 90, the computer captures pixels corresponding to regions located at equal angular increments around rotational sensing circle 200. Because the angular speed of rotation of optical assembly 30 is constant, the computer waits a predetermined period of time between the capture of each individual pixel, and thus, the computer captures pixels at a constant frequency.

The region on sample 90 corresponding to each pixel is characterized by (1) an angle a measured between reference line 220 and radius v at the time the computer captures the pixel and (2) the position of sample 90 as it moves in direction 95. Angle a and the length of radius v, define polar coordinates for each individual region in relation to the center of rotational sensing circle 200. These polar coordinates allow for easy translation to an orthogonal coordinate system, if desired.

Capturing pixels from regions at equal angular increments around rotational scanning circle 200 decreases the rectilinear space between regions on sample 90 as angle a increases to 90 degrees. Thus, regions corresponding to captured pixels near reference line 220 are spaced less tightly than regions located further from reference line 220. To ensure an adequate image with uniform resolution throughout, the computer may capture additional pixels, by increasing the frequency of pixel capture. These additional pixels may include pixels representing overlapping regions on sample 90, particularly for regions located near the edges of sample 90. The computer will then average these "oversampled" pixels together to create an image with a desired resolution. Pixels corresponding to regions near the center of sample 90 will not require averaging, while pixels captured as angle a increases will be oversampled and, thus, be averaged by the computer. Such oversampling and averaging procedure can counteract poor image quality that would otherwise result from the differences in distances between pixels. Accordingly, an image having a uniform resolution in a rectilinear coordinate system can be obtained. Using this oversampling correction, however, typically captures and averages a high number of samples taken as the angle between radius v and reference line 220 increases toward 90 degrees.

Figure 17B:
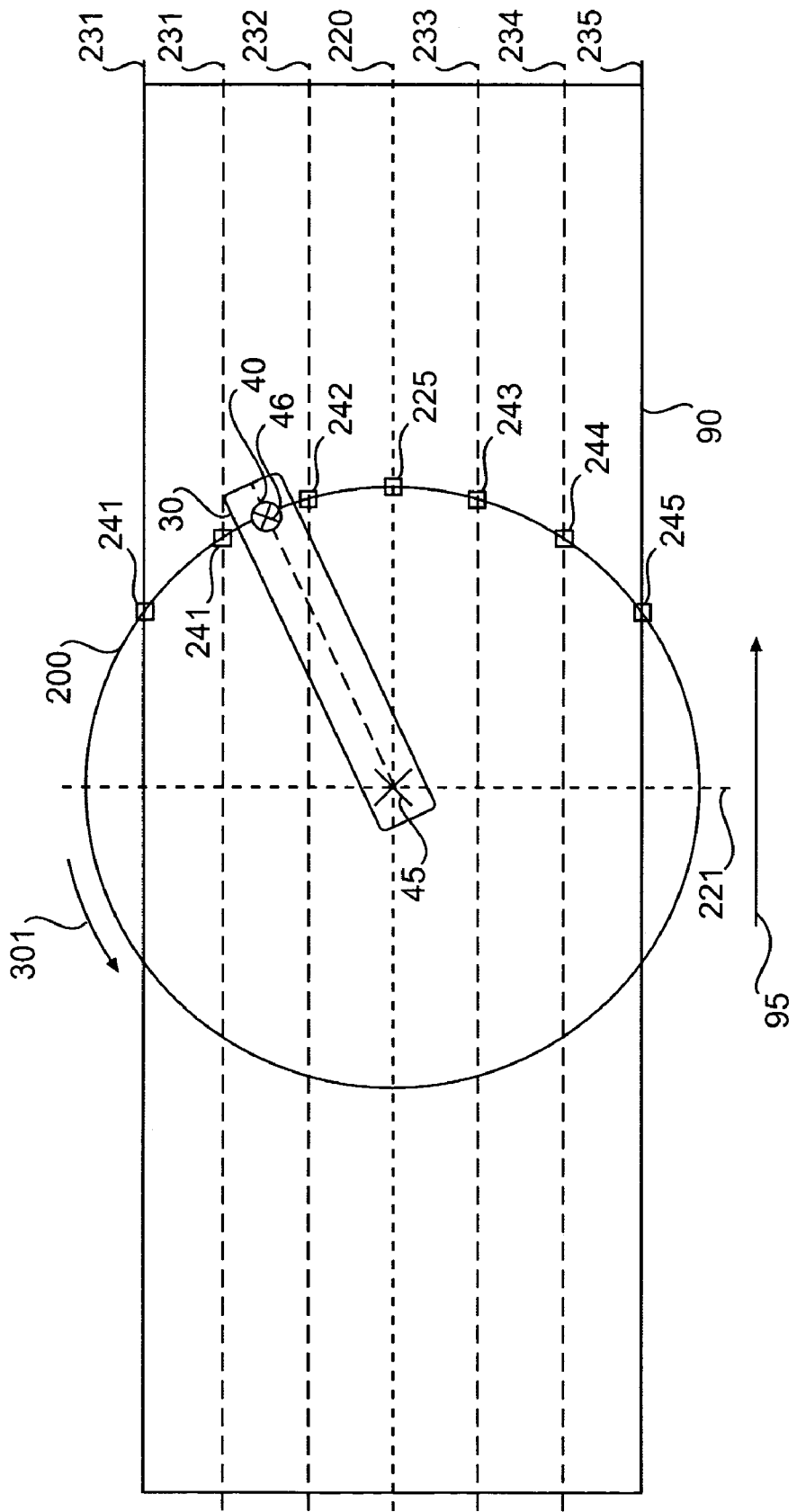

A second preferable method of creating an image of light emitted by sample 90 comprises detecting plural pixels corresponding to regions positioned at intersections of the rotational sensing circle 200 and a series of equidistant lines substantially parallel to reference line 220. FIG. 17B illustrates an example of a series of such equidistant lines 220 and 230-235. To sample light emitted by regions 225 and 240-245, detector 80 decreases the time it waits between capturing pixels as optical assembly 30 approaches the edges of sample 90. For example, detector 80 waits less time between detecting pixels corresponding to regions 244 and 245 than it does between pixels corresponding to regions 243 and 225. Using this method, sensing apparatus captures a set of pixels corresponding to regions distributed equidistantly in a direction parallel to reference line 221, simplifying translation to an orthogonal grid. Conversely, in a direction paralleling reference line 220, the regions have no uniform spacing and are further apart the further optical assembly 30 is from reference line 220. To create an image having uniform resolution, the computer interpolates the pixels it captures. To interpolate between a first and second pixel, the computer can, for example, read a portion of the first pixel closest to the second pixel, read a portion of the second pixel closest to the first pixel, and use the portions of the first and second pixels to approximate what the space between the first and second pixels should look like. The computer may also simply divide the first pixel, using a portion of it to approximate the image required for an adjacent pixel. Thus, as optical assembly 30 rotates closer to the edges of sample 90, the computer uses the captured pixels to create the desired image having a uniform resolution.

Figure 17C:
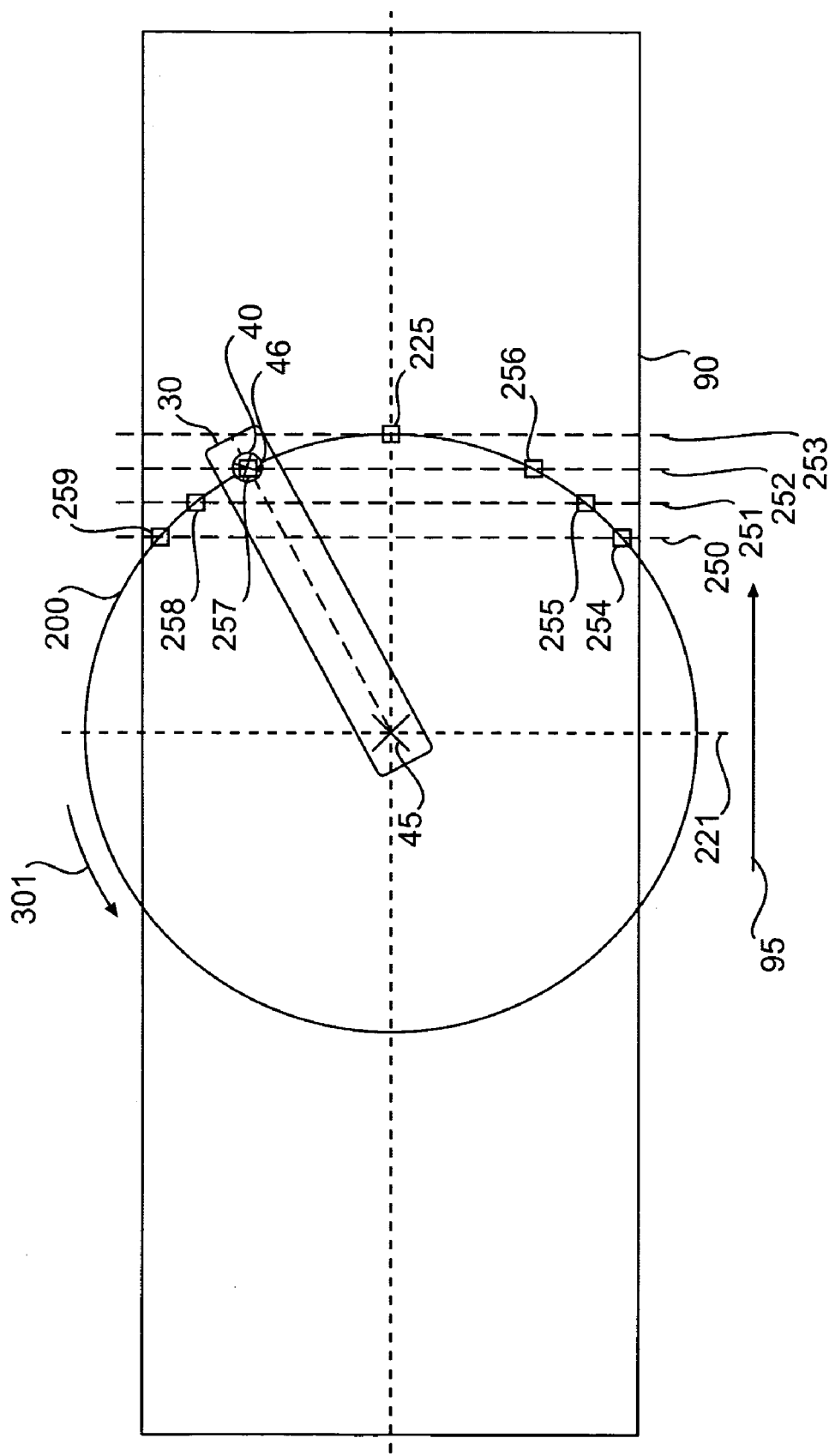

A third preferable method of creating an image of light emitted by sample 90, illustrated in FIG. 17C, also detects a plurality of pixels corresponding to regions positioned at the intersections of the rotational sensing circle 200 and a series of equidistant, substantially parallel lines 250-253, which are substantially parallel to reference line 221, not reference line 220. This method captures pixels corresponding to regions 225 and 255-259, which are distributed equidistantly in the in a direction paralleling reference line 220, but not in a direction paralleling reference line 221. Again, the computer interpolates between detected pixels when creating the image to create uniform resolution. Using either the second or third methods described herein requires comparatively less oversampling than the first method. FIGS. 17B and 17C illustrate only exemplary spacing of equidistant lines, and the sensing requirements of particular applications will dictate the required detailed of an image of the light emitted by sample 90, if any. Moreover, other imaging methods and pixels having a shape other than squares are contemplated herein.

Figure 2:
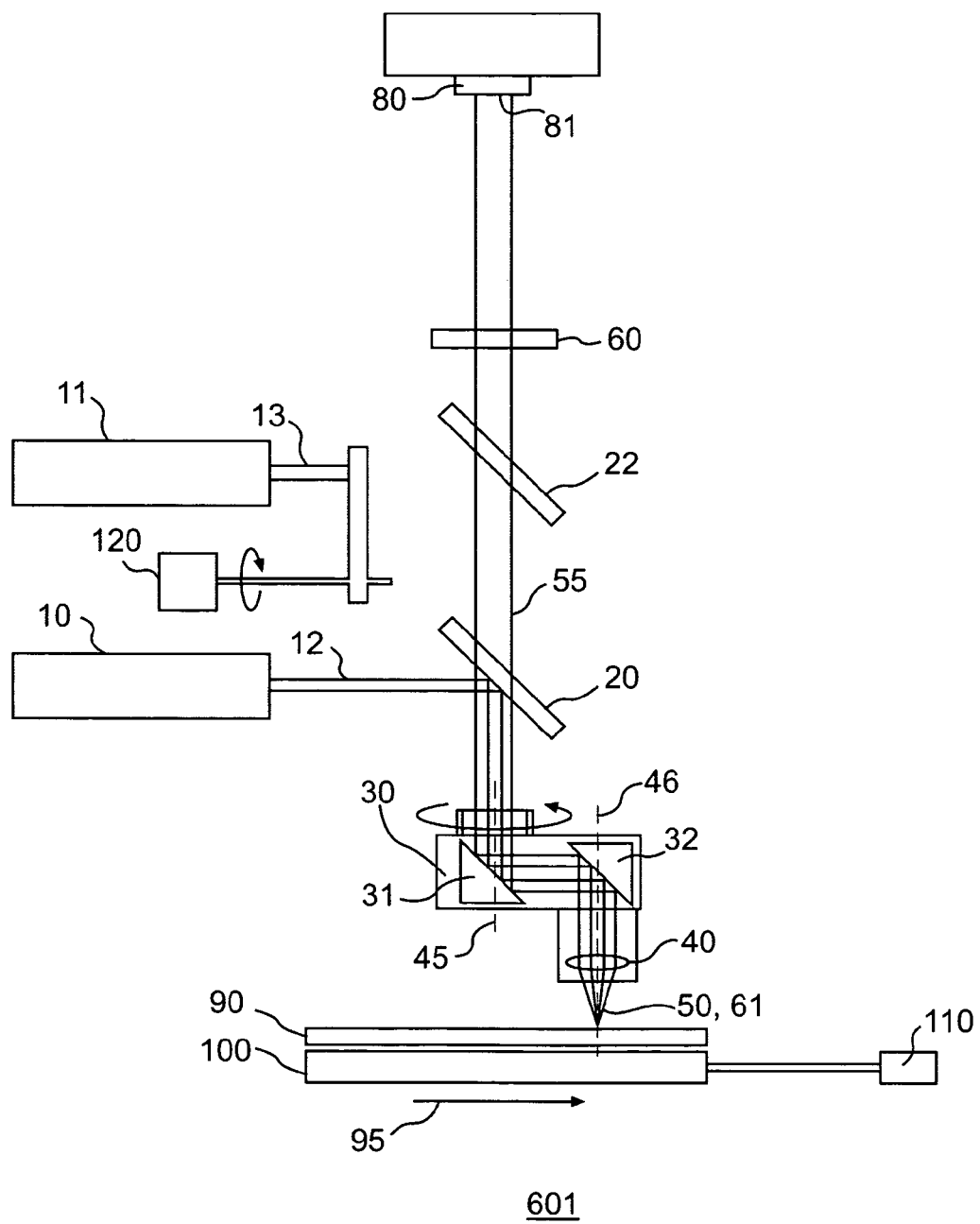
FIG. 2 is a schematic diagram of a second sensing apparatus consistent with an additional embodiment of the invention.

FIG. 2 illustrates sensing apparatus 601, also consistent with the present invention. Like sensing apparatus 600 described above, sensing apparatus 601 comprises an optical source 10, an optical filter 20, an optical assembly 30, an objective lens module 40, an optical filter 60, and a detector 80. In addition to these components, sensing apparatus 601 further comprises an optical source 11, an optical filter 22, and an optical chopper 120, which are described below.

Optical source 11 is a second optical source with characteristics similar to optical source 10. Preferably, optical source 11 includes a laser, which outputs excitation light 13 having a wavelength different than that of excitation light 12. In this configuration, excitation light 13 causes sample 90 to fluoresce and emit light 61, which has a wavelength different from the wavelength of the emitted light 50 emitted by sample 90 in response to excitation light 12. Thus, sample 90 emits light 50 at a first wavelength and emits light 61 at a second wavelength in response to exposure to excitation light 12 and excitation light 13, respectively.

As with excitation light 12, the optimal wavelength of excitation light 13 depends on sample 90. Persons of skill in the art typically use laser beams with different wavelengths to sense experimental results from samples including Cy3 dye and Cy5 dye, respectively. Because sensing apparatus 601 contains two optical sources 10, 11, it can sense samples dyed with two different dyes. Lasers suitable for use in optical source 11 are generally of the same type and grade as those suitable for use in optical source 10. Below, optical source 10 preferably includes a green laser, such as the LVY-VA-532-30 laser, and optical source 11 preferably includes a red laser, such as the LM-6535GR laser.

Alternatively, Optical source 10 and optical source 11 can include lasers producing light having the same wavelength. In this alternative configuration, for example, optical source 10 and optical source 11 could each include a green laser. In this configuration, sensing apparatus 601 would be used to sense samples dyed with a single dye. As will be explained below, using two optical sources, as in sensing apparatus 601, as opposed to a single optical source, as in apparatus 600, allows the sensing apparatus to sense all desired results on a given sample more quickly.

Optical filter 22, like optical filter 20, is configured to reflect light having a particular wavelength, but allows light having other wavelengths to pass through. In particular, optical filter 22 preferably has a coating, which reflects excitation light 13, but allows emitted light 50, 61 to pass through. Preferably, Optical filter 20 is the Q555Ip optical filter, commercially available from Chroma Technology Corporation. Optical filter 22 is preferably the 61005bs optical filter, also available from Chroma Technology Corporation.

As further shown in FIGS. 2 and 8, sensing apparatus 601 includes an optical chopper 120, which comprises a light-interruption plate mounted substantially perpendicular to a rotating shaft. Optical chopper 120 is configured to allow one of excitation light 12 or excitation light 13 to reach sample 90 at a time. As it rotates, optical chopper 120 moves from a position that interrupts excitation light 12 to a position that interrupts excitation light 13 and back again. In this manner, each of excitation light 12 and excitation light 13 are directed to sample 90 for a portion of time, such that excitation light 12 and excitation light 13 do not simultaneously expose the same location on sample 90. Preferably, optical chopper 120 rotates at the same rate as optical assembly 30.

As mentioned above, optical chopper 120 prevents excitation light 12 and excitation light 13 from simultaneously exposing the same location on sample 90. Thus, optical chopper 120 enables detector 80 to distinguish emitted light 50, emitted in response to excitation light 12, from emitted light 61, emitted in response to excitation light 13. Optical chopper 120 may also be provided in a sensing apparatus having multiple detectors, as discussed below and illustrated in FIG. 3.

FIG. 7 illustrates two exemplary light-interruption plates for use as optical chopper 120 consistent with the present invention. Light-interruption plate 122, illustrated in FIG. 7A, is fixed to, and rotates with, shaft 121. An open region 123 allows one of excitation light 12 or excitation light 13 to pass through light-interruption plate 122. Rotating shaft 121 causes light-interruption plate 122 to rotate to a particular position where the other of excitation light 12 or excitation light 13 passes through open region 123.

Light-interruption plate 125, illustrated in FIG. 7B, has a semicircular shape. Light-interruption plate 125 is fixed to shaft 121, with which it rotates. Rotating shaft 121 causes light-interruption plate 125 to rotate about the shaft, interrupting one of excitation light 12 or excitation light 13 at a given time.

Optical chopper 120 may also include a light-interruption plate having a different shape than those described above. If sensing apparatus 601 were, for example, to comprise more than two light sources, an optical chopper having a shape other than a semicircle would be desirable. Moreover, it is possible to use plural optical choppers in a sensing apparatus.

Of course, it is possible, and may be preferable in some instances, to allow excitation light 12 and excitation light 13 to reach a single location on sample 90 at the same time. Eliminating chopper 120 from apparatus 601 would bring allow both excitation light 12 and excitation light 13 to irradiate a location on sample 90 simultaneously. Generally, however, it is preferable to include chopper 120, or other known components, to allow only one of excitation light 12, 13 to reach a location on sample 90 at a time.

Operation of sensing apparatus 601 will now be described, with reference to FIGS. 2 and 8.

Figure 8A:
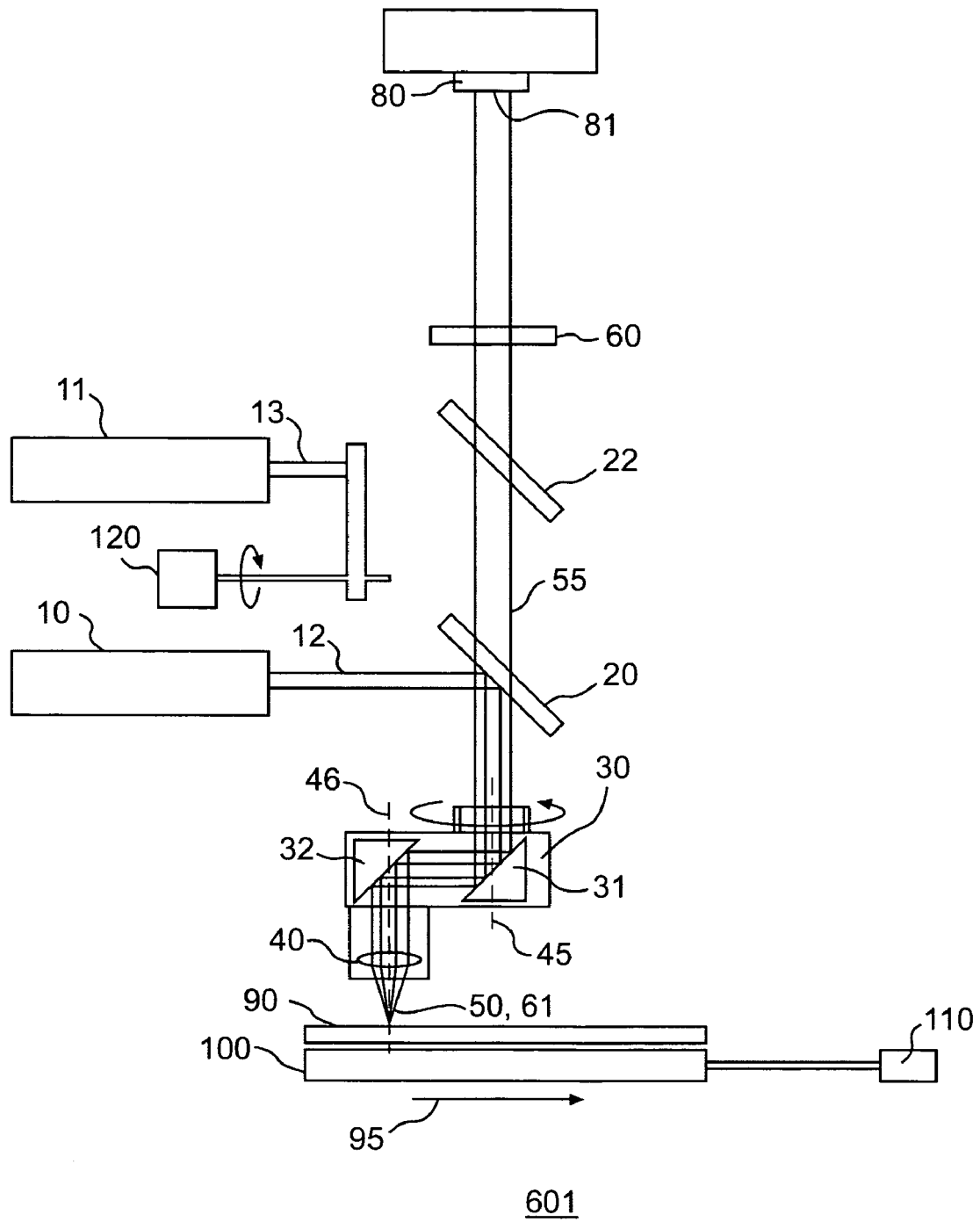
FIGS. 8A and 8B are schematic diagrams of the sensing apparatus illustrated in FIG. 2.

At a first point in time, optical source 10 outputs excitation light 12, which reflects off of optical filter 20, is received by optical assembly 30, and is focused and directed to a first location 91 on sample 90 by objective lens assembly 40, as illustrated in FIGS. 8A and 4A. Chopper 120 interrupts excitation light 13, preventing it from reaching sample 90.

Sample 90 emits light 50 having a first wavelength in response to excitation light 12. Emitted light 50 passes through objective lens module 40, which collimates emitted light 50 into beam 55. Beam 55 substantially passes through optical filters 20, 22, and 60 before reaching detector 80.

Figure 8B:
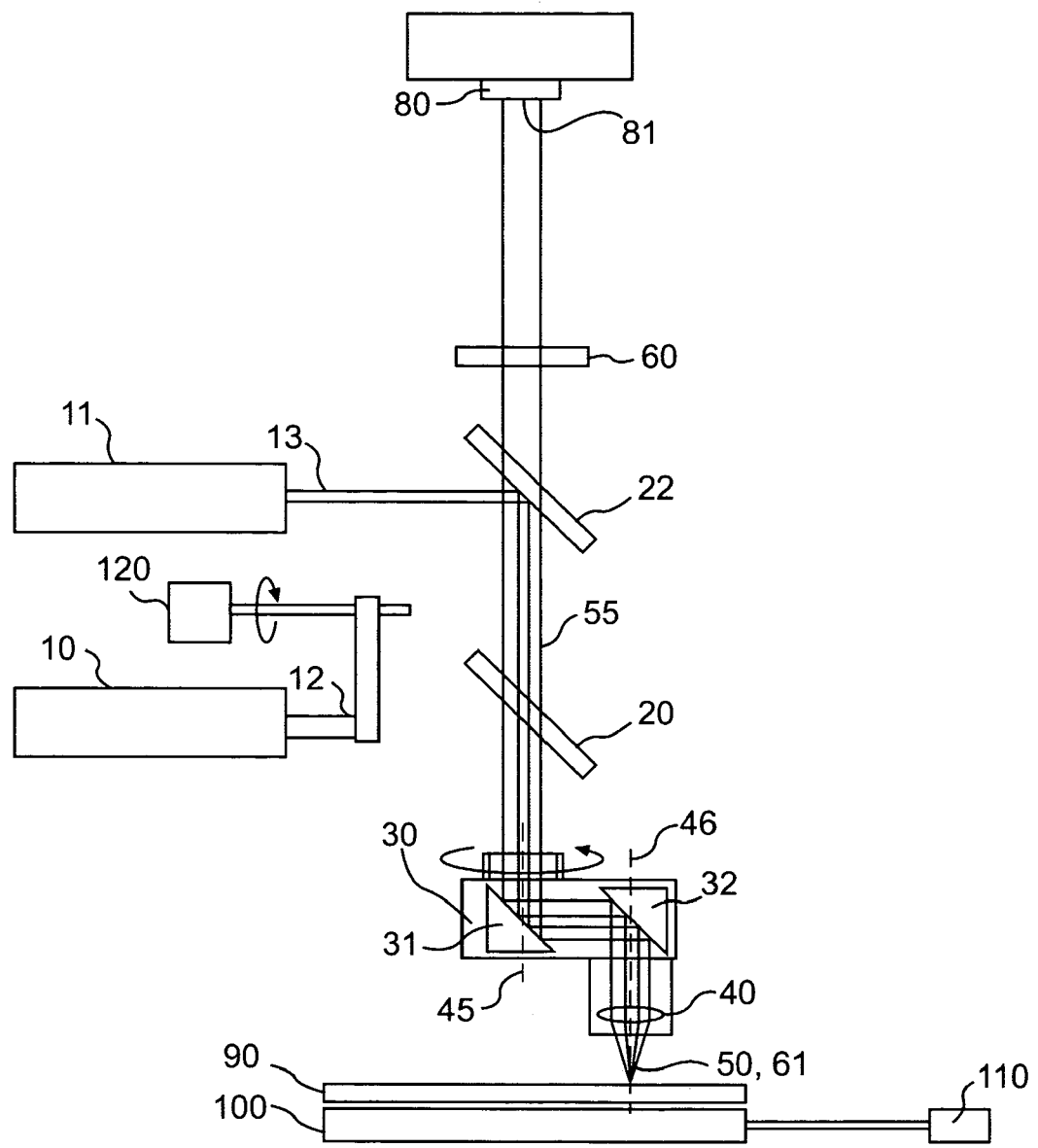

At a second point in time, as illustrated in FIG. 8B, chopper 120 moves to a second position, at which optical chopper allows excitation light 13 to pass, but interrupts excitation light 12. At this second point in time, optical assembly 30 has rotated about axis 45 to a second position, as illustrated in FIGS. 8B and 4B. In this instance, excitation light 13 is output by optical source 11, reflects off of optical filter 22, passes through optical filter 20, optical assembly 30, and objective lens module 40, and reaches a second location 92 on sample 90.

Sample 90 emits light 61 having a second wavelength in response to excitation light 13. Objective lens module 40 collimates emitted light 61 into beam 55. Beam 55 substantially passes through optical filters 20, 22, and 60 before reaching detector 80. In sensing apparatus 601, optical filter 20 is configured to allow light having the wavelengths of excitation light 13, emitted light 50, and emitted light 61 to pass through it. Optical filter 20, however, is configured to reflect light having the wavelength of excitation light 12. Optical filter 22 is configured to reflect light having the wavelength of excitation light 13, but is configured to allow light having the wavelengths of emitted light 50, 61 to pass. Thus, after passing through optical filters 20 and 22, beam 55 should contain substantially only light emitted by sample 90. To further reduce the amount of excitation light 12 and excitation light 13 that may reach detector 80, optical filter 60 is optionally provided to further attenuate wavelengths other than those emitted by sample 90.

Detector 80, as used in sensing apparatus 601, detects both wavelengths of light emitted by sample 90, and typically cannot distinguish emitted light 50 from emitted light 61. Optionally, however, sensing apparatus 601 may employ additional equipment to discriminate between the two optical signals. For example, a computer controlling detector 80 may use the rate at which chopper 120 rotates to determine whether detector 80 received emitted light 50 or emitted light 61 at a particular time. By correlating the light received by detector 80 with the excitation light 12, 13 incident on sample 90 at that time, the computer can determine what materials were present on sample 90.

As illustrated, for example, in FIG. 2, preferably sample 90 moves in a linear direction 95 in relation to axis 45 of optical assembly 30. In FIG. 2, sample 90 and sample holder 100 move in direction 95 while the remainder of sensing apparatus 601 remains substantially stationary, other than the rotation of optical assembly 30 and optical chopper 120. Sample 90, however, may remain stationary while rotating optical assembly 30 moves in a linear direction relative to sample 90. In either case, the speed of the linear relative movement of sample 90 and axis 45 preferably remains constant and slow compared to the rotational speed of optical assembly 30.

Figure 10:
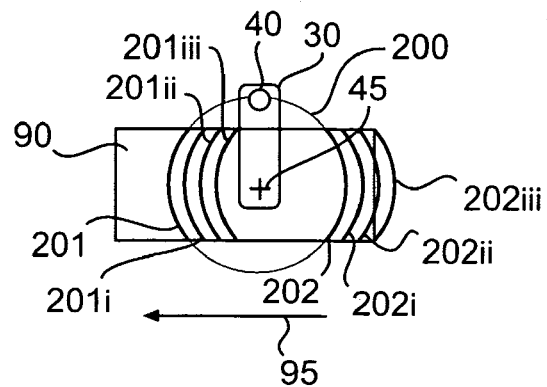
FIG. 10 is a schematic-diagram of a rotational sensing circle consistent with sensing apparatuses consistent with embodiments of the invention.

As described above and illustrated, for example, in FIG. 10, the rotation of optical assembly 30 about axis 45 defines rotational sensing circle 200. The radius of rotational sensing circle 200 extends from axis 45 to axis 46. Preferably, rotational sensing circle 200 has a diameter larger than a width of sample 90 perpendicular to direction of the linear relative motion represented by arrow 95 in FIG. 10.

Over time, the relative motion of sample 90 and axis 45 causes each location on sample 90 to be illuminated by a leading arc 201 of the rotational sensing circle 200, a trailing arc 202 of the rotational sensing circle 200, or by both leading arc 201 and trailing arc 202. "Leading" arcs and "trailing" arcs typically occupy substantially opposite sides of sensing circle 200, and are located such that the direction of linear relative motion of sample 90, shown by arrow 95 in FIG. 10, points from the "trailing" arc toward the "leading" arc. For example, arrow 95 points from trailing arc 202 toward leading arc 201 in FIG. 10. By illuminating multiple regions on sample 90 and capturing pixels corresponding to light detected from each region on sample 90, sensing apparatus 601 can create an image of the light emitted by sample 90 using one of the methods described with regard to sensing apparatus 600 above.

The linear relative movement of sample 90 with respect to rotational sensing circle 200 will cause sensing apparatus 601 to illuminate sample 90 with a sequence of leading arcs 201$i$, 201$ii$, 201$iii$, and a series of trailing arcs 202$i$, 202$ii$, and 202$iii$. The distance between consecutive arcs, such as leading arcs 201$i$, 201$ii$, and 201$iii$, depends on the number of revolutions of the focal point of objective lens assembly 40 per unit length of the linear relative movement in direction 95. The displacement between consecutive arcs, such as leading arcs 201$i$, 201$ii$, and 201$iii$, defines the resolution of sensing apparatus 601 in direction 95.

Varying the combination of excitation light 12, 13 present when leading arc 201 and trailing arc 202 pass over sample 90, provides several operational modes for sensing apparatus 601. These different operational modes, examples of which are illustrated in FIGS. 11-15 and described below, provide different ways to provide excitation light 12, 13 to all locations on sample 90. In each mode of operation, sample 90 is completely covered by illuminated arcs, or parts of arcs, stemming either from the leading arc 201, trailing arc 202, or both in combination. Allowing only one of excitation light 12, 13 to reach sample 90 during the complete scanning operation constitutes single-channel scanning. Conversely, allowing both excitation light 12 and excitation light 13 to reach sample 90, whether simultaneously, in sequence, or another combination, during the complete scanning operation constitutes dual-channel scanning. Persons of skill in the art will appreciate that adding more excitation sources will similarly provide for increasing levels of multi-channel scanning.

In each of the exemplary operational modes described below, sensing apparatus 601 directs excitation light 12 and/or excitation light 13 to sample 90 and detects emitted light 50 and/or emitted light 61 from sample 90. To simplify the discussion herein, the description of FIGS. 11-15 below describes only the illumination of sample 90. It is to be understood, however, that these exemplary operational modes also allow for the detection of light emitted by sample 90 using detector 80.

Figure 11:
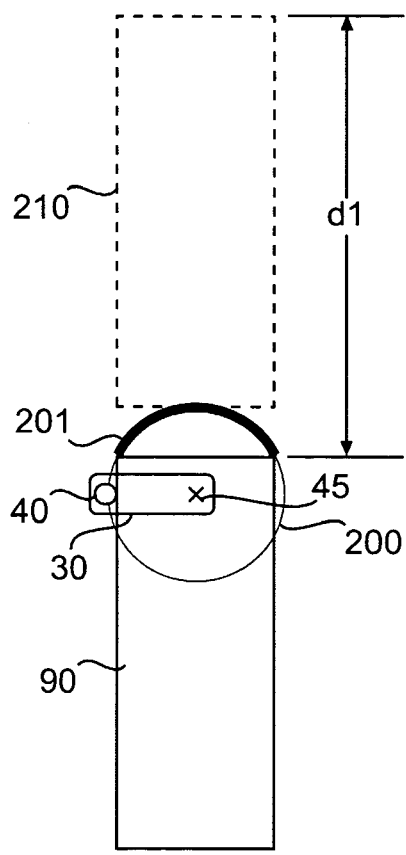

FIG. 11 illustrates a "normal" single-channel mode, in which excitation light 12 illuminates sample 90 only during leading arc 201. When sensing apparatus 601 operates in the normal single channel mode, excitation light 13 is not supplied to sample 90 during any portion of the full rotational sensing circle 200. Exposing all locations on sample 90 to excitation light 12 requires relative linear relational movement of sample 90 and axis 45 over a distance d1. This relative linear movement causes sample 90 to move from a first position, which FIG. 11 indicates with solid lines, to a second position, shown with dashed lines 210.

An alternate normal single-channel mode is provided by illuminating sample 90 with excitation light 13 during the leading arc 201, but not exposing sample 90 to excitation light 12 during the entire rotational sensing circle 200. Moreover, replacing the leading arc 201 with the corresponding trailing arc 202 will require a length of linear relational movement equal to distance d1 to completely illuminate sample 90. Sensing Apparatus 600, which comprises a single optical source, can also operate in the normal single-channel mode shown in FIG. 11.

When the number of revolutions per unit of linear relational movement remains constant, distance d1 is directly proportional to the time required to expose all locations on sample 90 to excitation light 12. The same relationship between time and total relative linear movement exists for the operational modes illustrated in FIGS. 12, 13, 14, and 15, if the number of revolutions per unit of linear relational movement remains constant. Comparing the distance traveled by sample 90 in each of these figures allows a comparison of the time necessary to illuminate all locations on sample 90 with excitation light using different operational modes for sensing apparatus 601. Namely, requiring sample 90 to travel a longer distance, corresponds to more time required to expose all of sample 90 to excitation light.

Figure 12:
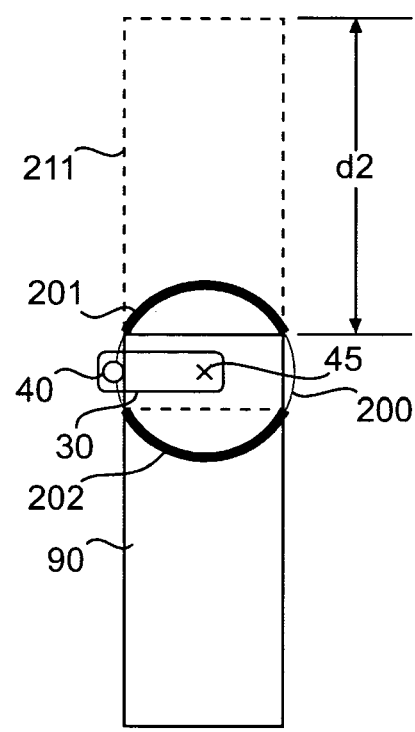

FIG. 12 illustrates a "fast" single-channel mode, where excitation light 12 reaches sample 90 during both the leading arc 201 and trailing arc 202. As in the normal single channel mode illustrated in FIG. 11, excitation light 13 is not sent to sample 90 at any time during the operation of sensing apparatus 601. Sending excitation light 12 to all locations on sample 90 requires linear relational movement of sample 90 and axis 45 over a distance d2, moving sample 90 to the position indicated by dashed lines 211 in FIG. 12.

As mentioned above, when the number of revolutions per unit of linear relational movement remains constant, the distance traveled by sample 90 is directly proportional to the time required to expose all locations on sample 90 to illumination light 12, 13. Since sample 90 is exposed to excitation light 12 over both leading arc 201 and trailing arc 202 (FIG. 12), more of sample 90 is exposed during each rotation of optical assembly 30 than if exposed over only leading arc 201 (FIG. 11). Thus, distance d1, the distance traveled by sample 90 in FIG. 11, is greater than distance d2, the distance traveled by sample 90 in FIG. 12. Sensing Apparatus 600, which comprises a single optical source, can also operate in the fast single-channel mode shown in FIG. 12.

Figures 13A, 13B:
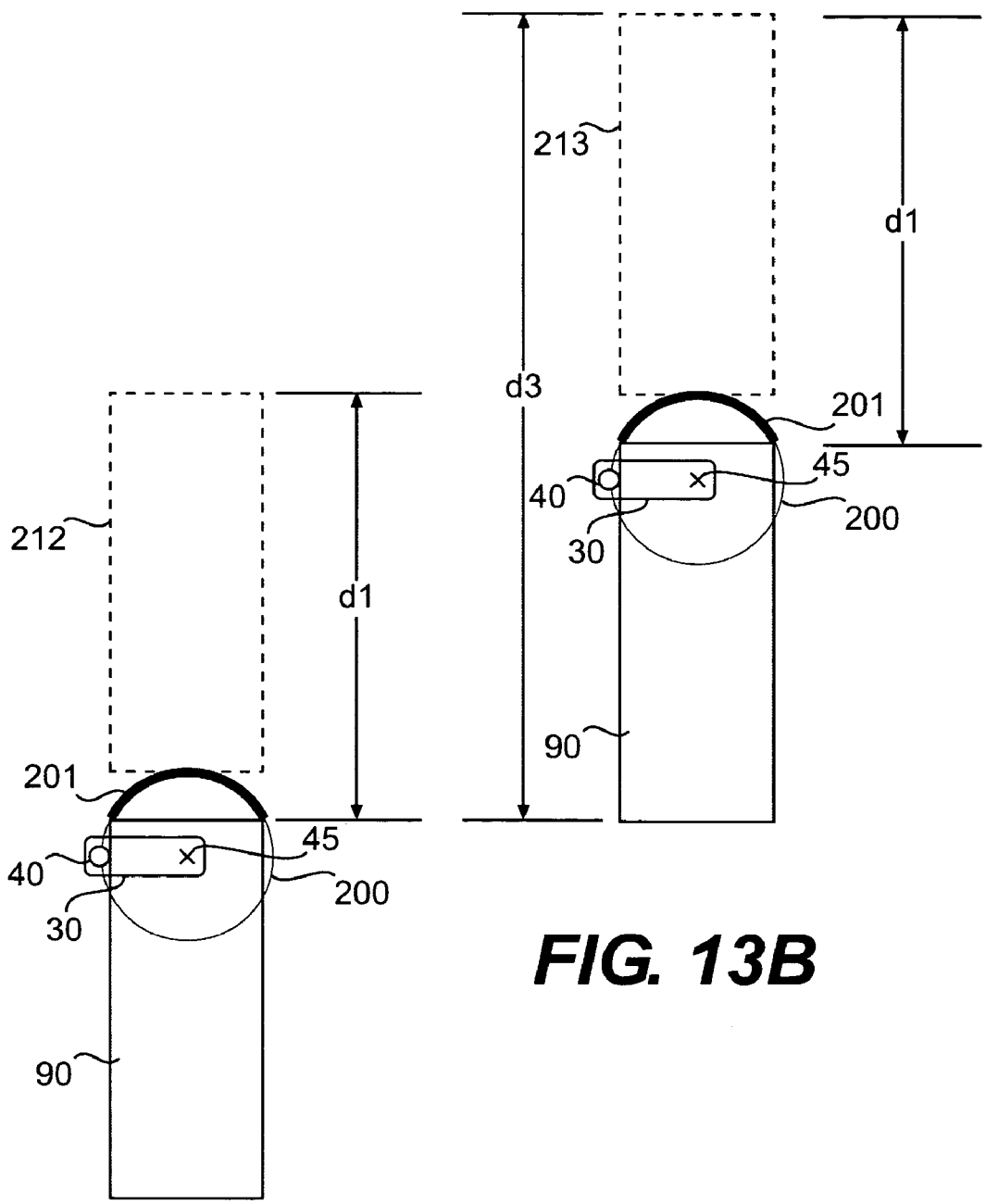

Together, FIGS. 13A and 13B illustrate a normal dual-channel mode, showing, in FIG. 13A, the complete illumination of sample 90 in one of the two normal single-channel modes described above, followed by a complete scanning of sample 90 in the other of the two normal single-channel modes described above in FIG. 13B. In this manner, sensing apparatus 601 senses sample 90 using both optical source 10 (in FIG. 13A) and optical source 11 (in FIG. 13B). The length of the complete dual channel scan is distance d3, being twice the distance d1.

During the first sensing operation, sample 90 moves from its original position to a second position, shown by dashed lines 212 in FIG. 13A. The sample subsequently moves to a third position, represented by dashed lines 213 in FIG. 13B. Sample 90 is not, however, limited to the movement illustrated in FIGS. 13A and 13B. The movement required by the normal dual-channel mode may be accomplished using two separate sensing apparatuses 601 (or sensing apparatuses 600). Alternatively, sample 90 may be moved in a first linear direction during the first sensing operation and moved in the opposite the direction during the second sensing operation. Moreover, the normal dual-channel mode can be accomplished by performing the first sensing operation on sample 90, then moving sample 90 back to its original position before beginning the second sensing operation. No matter which of these movements of sample 90 is used, sample 90 will move an entire distance d3 while being sensed.

The normal dual-channel mode of operation has several disadvantages relative to other modes of operating sensing apparatus 601. In particular, the normal dual-channel mode of operation is the slowest of the dual-channel modes. Moreover, the sequential illumination of locations on sample 90 with excitation light 12, 13 are delayed relative to one another, providing the possibility of excitation source or detector drift. The normal dual-channel mode, however, has the advantages of avoiding crosstalk between channels and using a single detector 80 instead of separate detectors for light emitted in response to each of excitation light 12, 13. (A sensing apparatus 602 having multiple detectors 80, 81 will be discussed below.)

When operating in the fast dual-channel mode, illustrated in FIG. 14, sensing apparatus 601 first illuminates sample 90 using one of the two fast single-channel modes described above (for example with optical source 10) and then illuminates sample 90 in the other of the two fast single-channel modes described above (for example with optical source 11). Sample 90 moves from its initial position to the position indicated by dashed lines 214 in FIG. 14A, and then to the position indicated by dashed lines in FIG. 14B. As with the normal dual-channel mode discussed above, sample 90 is not limited to the particular motion illustrated in FIGS. 14A and 14B. The movement of sample 90 may be accomplished by reversing its direction, returning sample 90 to its original position before beginning the second sensing operation, using multiple sensing apparatuses, or other methods.

In this fast dual-channel mode, sample 90 moves a total distance d4, which is twice the distance d2. Distance d4 is less than distance d3, and thus sample 90 can be sensed faster by using two fast single-channel modes in sequence than using two successive normal single-channel modes.

In the fast dual-channel mode of operation, a delay exists between sequential illuminations of locations on sample 90 with excitation light 12, 13 relative to one another, creating the possibility of excitation source or detector drift. Because only excitation light 12 or excitation light 13 illuminates sample 90 during each sensing of sample 90, the fast dual-channel mode eliminates potential crosstalk between channels and requires only a single detector 80 instead of dual matched detectors. Moreover, the fast dual-channel mode of operation completes its sensing operation more quickly than the normal dual-channel mode discussed above.

Figure 15:
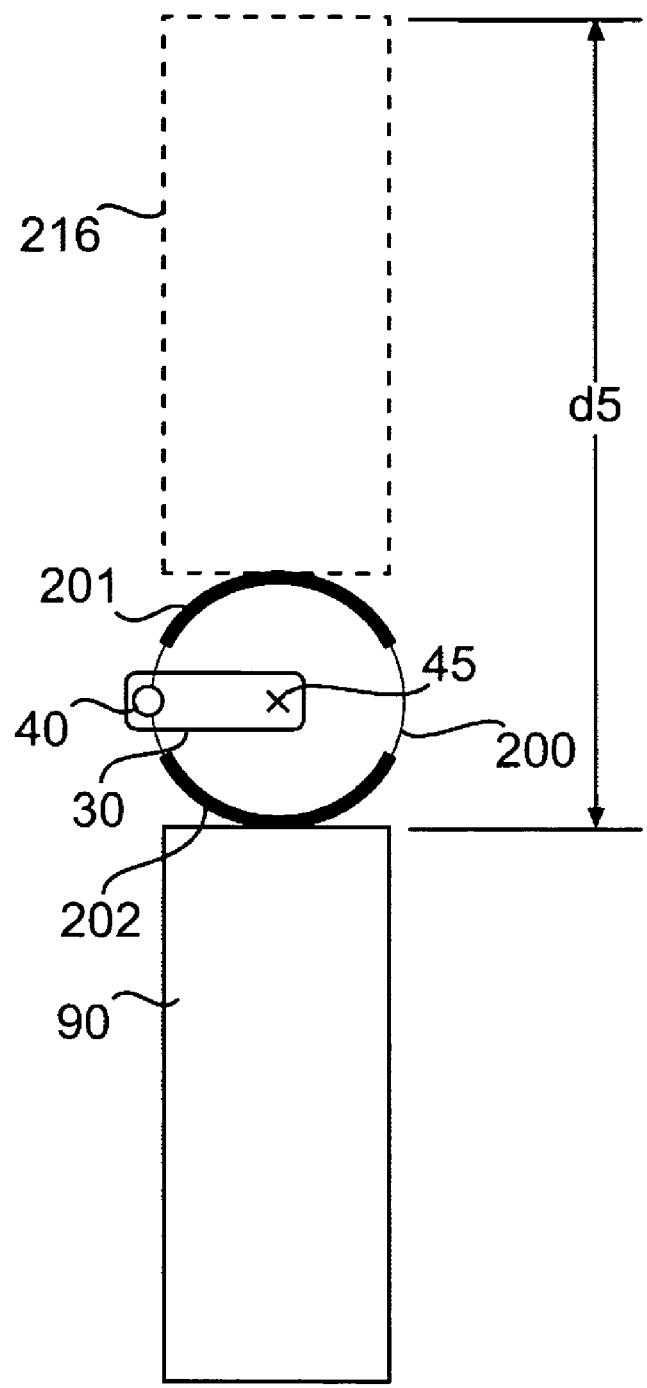

FIG. 15 depicts an overlaid dual-channel mode. When sensing apparatus 601 operates in this overlaid dual-channel mode, excitation light 12 exposes sample 90 during leading arc 201 and excitation light 13 exposes sample 90 during trailing arc 202. To completely illuminate all locations on sample 90 in this mode of operation, sensing apparatus 601 requires a linear relational movement over distance d5, moving sample 90 to the position indicated by dashed lines 216 in FIG. 15. Moving sample 90 in this manner provides two separate complete illuminations of sample 90, each covering sample 90 completely by arcs, or parts of arcs. Because excitation light 12 exposes sample 90 during leading arc 201 and excitation light 13 exposes sample 90 during trailing arc 202, all locations on sample 90 receive both excitation light 12 and excitation light 13.

Distance d5 is less than either distance d3 or distance d4. Thus, using the overlaid dual-channel mode provides faster illumination of all locations on sample 90 than using either the normal dual-channel mode or the fast dual-channel modes. Another advantage of the overlaid dual-channel mode is the absence of crosstalk between channels during scanning, as leading arc 201, which illuminates sample 90 with excitation light 12, and trailing arc 202, which illuminates sample 90 with excitation light 13, are physically displaced from each other. A possible disadvantage of the overlaid dual-channel mode is the preexposure of sample 90 by excitation light 12 during the leading arc 201 in relation to the following displaced scanning by the excitation light 13 during the trailing arc 202.

An interleaved dual-channel mode will now be described with reference to FIG. 12. In this interleaved dual-channel mode, excitation light 12 reaches sample 90 during both the leading arc 201 and the trailing arc 202 during a first revolution of the objective lens assembly 40. Excitation light 13 does not expose sample 90 during this first revolution of objective lens assembly 40. In a second revolution of objective lens assembly 40, however, the on/off status of optical sources 10 and 11 is switched. Thus, during, the second revolution of objective lens assembly 40, excitation light 13 illuminates sample 90, but excitation light 12 does not. Preferably, the first and second revolutions represent consecutive revolutions of objective lens assembly 40, and the pattern is repeated so that sensing apparatus 601 creates two complete sensings of sample 90 based on alternating revolutions, each of the two sensings being illuminated by a different one of the two excitation lights 12, 13.

Using this operational mode, sample 90 moves a distance d2, from its original position to the position indicated by dashed lines 211.

Because the arcs are interleaved in the manner described above, this operational mode results in half of the resolution of the other dual scanning operational modes. To compare the interleaved dual-channel mode to the other dual scanning modes, therefore, it is necessary to double distance d2. Doubling distance d2 results in a distance equal to distance d4, shown in FIG. 14.

The interleaved dual-channel operational mode provides a sensing speed equal to that of the fast dual-channel mode. The dual channel operational mode does not, however, create a significant time span between the sensing of each channel. Thus, little drift of the excitation sources and detector occurs between channel scans when using the interleaved dual-channel operational mode.

Finally, FIG. 12 can also be used to describe a simultaneous dual-channel operational mode. In this simultaneous dual channel operational mode, sensing apparatus 601 illuminates sample 90 with both excitation light 12 and excitation light 13 turned on during both the leading arc 201 and the trailing arc 202. As detector 80 will not separate emitted light 50 from emitted light 61, the output from sensing apparatus 601 will represent the sum of fluorescence resulting from both excitation light 12 and excitation light 13.

When operating in this simultaneous dual-channel operational mode, sensing apparatus 601 only requires sample 90 to move over distance d2.

Distance d2 is less than distance d3, distance d4, and distance d5, indicating that using the simultaneous dual-channel operational mode is faster than either of the other dual-channel modes. It is noted, however, that not all applications are suited to work with only a single combined output from the two excitation sources.

FIG. 9 illustrates sensing apparatus 603, consistent with further aspects of the invention. Sensing apparatus 603 comprises the same components as sensing apparatus 601, except for blocking filters 130, 131 are provided instead of chopper 120.

Blocking filter 130 preferably is configured to block light having the wavelength of excitation light 12, while blocking filter 131 preferably blocks light having the wavelength of excitation light 13. Blocking filters 130, 131, when combined with the rotation of optical assembly 30 about axis 45, allow only one of excitation light 12, 13 to reach sample 90 at a time.

Figure 9A:
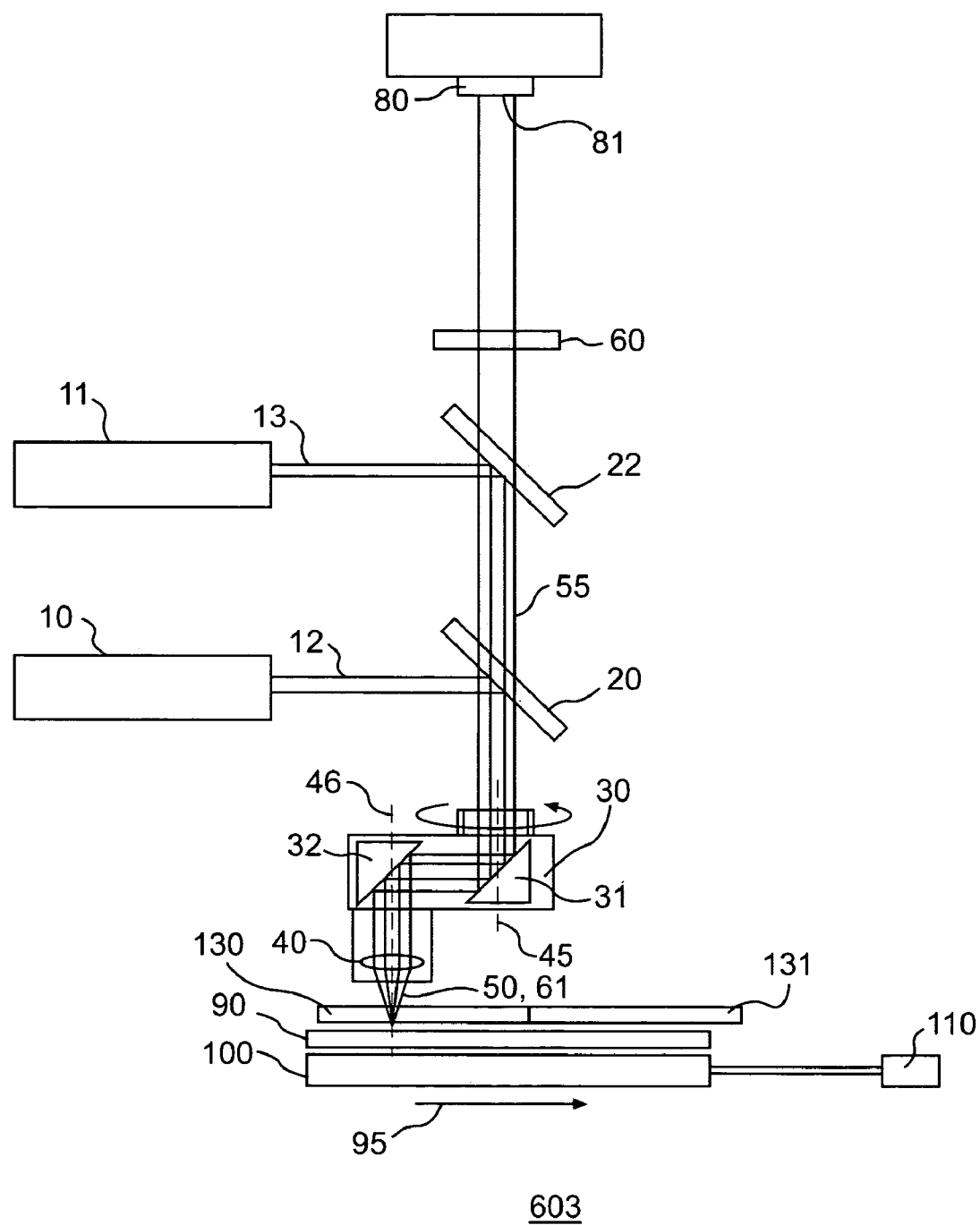
FIGS. 9A and 9B are schematic diagrams of a variation of the sensing apparatus illustrated in FIG. 2, consistent with an embodiment of the invention.
Figure 9B:
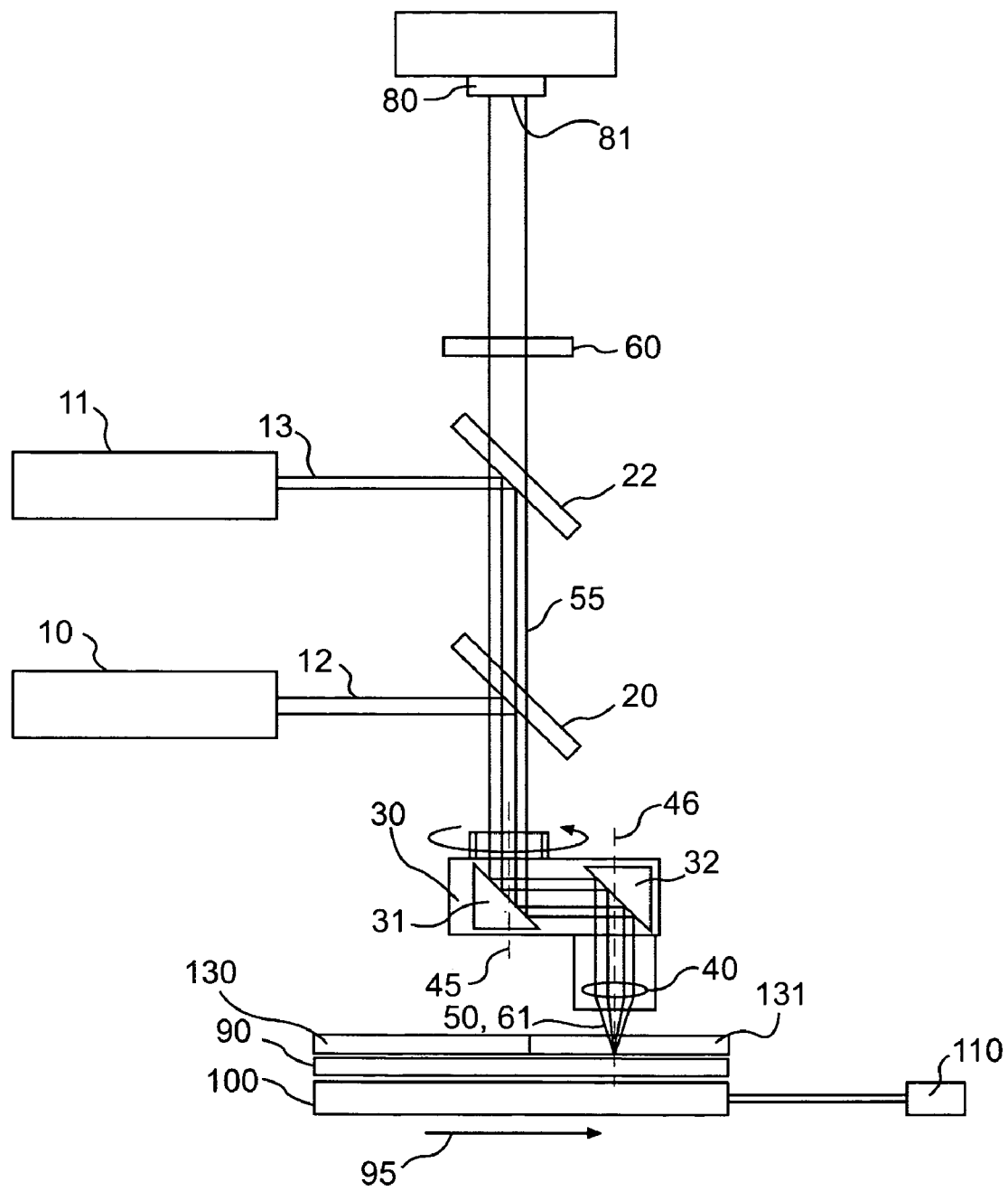

As illustrated in FIG. 9A, for example, at a first point in time when optical assembly is in a first position, blocking filter 130 prevents excitation light 11 from reaching sample 90. At a second point in time after optical assembly 130 rotates to a second position, blocking filter 131 prevents excitation light 13 from reaching sample 90, as illustrated in FIG. 9B. In this manner, blocking filters 130, 131 allow only one of excitation light 12, 13 to reach sample 90 at any given time.

Blocking filters 130, 131 constrain the operational modes available to sensing apparatus 603, as blocking filters 130, 131 effectively limit leading arc 201 to one of excitation light 12, 13 and trailing arc 202 to the other of excitation light 12, 13. Thus, blocking filters 130, 131 prevent the use of the fast single-channel mode, the normal dual-channel mode, the fast dual-channel mode, and the interleaved dual-channel mode. Sensing apparatus 603 can, however, operate in the normal single-channel mode and the overlaid dual-channel operation mode.

Figure 3:
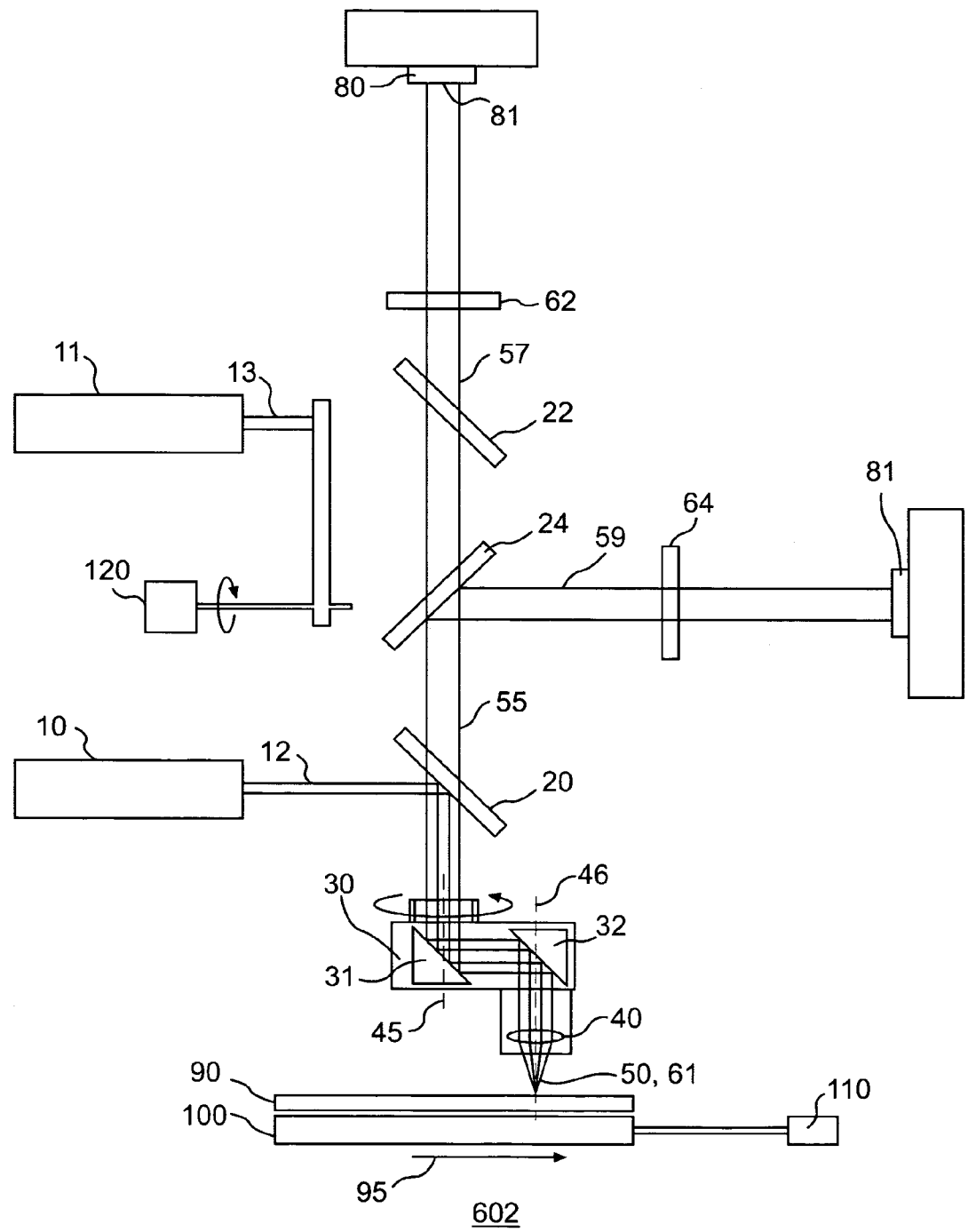
FIG. 3 is a schematic diagram of a third sensing apparatus consistent with a further embodiment of the invention.

FIG. 3 illustrates sensing apparatus 602, consistent with further aspects of the present invention. As illustrated in FIG. 3, sensing apparatus 602 comprises the same components as sensing apparatus 601. Sensing apparatus 602, further comprises, however, additional optical filters 24, 64, and an additional detector 81.

In sensing apparatus 602, optical filter 24 separates beam 55 into beam 57 and beam 59, by reflecting emitted light 61 to form beam 59, for example, while passing emitted light 50 to form beam 57. As a result, emitted light 50 is directed toward detector 80 and emitted light 61 is directed toward detector 81.

Optical filter 64 is configured to attenuate unwanted wavelengths of light from the beam 59 before it reaches detector 81. Optical filter 64 operates in a manner similar to optical filter 62, described above.

The beam of emitted light 61 is converted to corresponding electrical signals by detector 81, which a user or computer can store and/or analyze. Like detector 80, detector 81 preferably comprises a PMT detector. Because objective lens module 40 collimates emitted light 61, detector 81 can adequately detect the florescence of sample 90. Instead of scattering, the photons in the collimated beam 59 travel substantially parallel to one another. Preferably, the beam of collimated emitted light 61 substantially covers an area comprising the light-sensing opening of detector 81, allowing detector 81 to convert it into appropriate electrical signals from which information concerning sample 90 can be obtained.

Like sensing apparatuses 600 and 601, sensing apparatus 602 can create an image representing the light emitted by sample 90 by illuminating multiple regions on sample 90 and capturing pixels corresponding to light detected from each region. Moreover, sensing apparatus 602 can operate in any of the operational modes described above with respect to sensing apparatus 601.

Because sensing apparatus 602 contains two separate detectors 80, 81, however, sensing apparatus 602 can operate in an additional operational mode not discussed above, the separate simultaneous dual-channel mode, to be described with reference to FIG. 12. The separate simultaneous dual-channel mode allows illumination of sample 90 with both excitation sources turned on during both the leading arc 201 and the trailing arc 202. Due to the presence of multiple detectors 80, 81, sensing apparatus 602 can distinguish emitted light 50 from emitted light 61. Sensing apparatus 602 can thus output two simultaneous, complete sensings of sample 90, one from each detector 80, 81.

In this operational mode, sample 90 only moves a distance d2 relative to axis 45. The separate simultaneous dual-channel mode is as fast or faster than any of the other dual-channel modes described above. Moreover, the separate simultaneous dual-channel mode has the additional advantage of using separate detectors 80, 81 for each channel, making it able to functionally replace any of the other dual-channel modes of operation.

The presence of separate detectors 80, 81, however, makes sensing apparatus 602 prone to crosstalk between channels. Moreover, sensing apparatus 602 requires more components than sensing apparatus 601, including additional detector 81, and additional optical filters 24, 64. The presence of these additional components increases manufacturing and maintenance costs.

Figure 16:
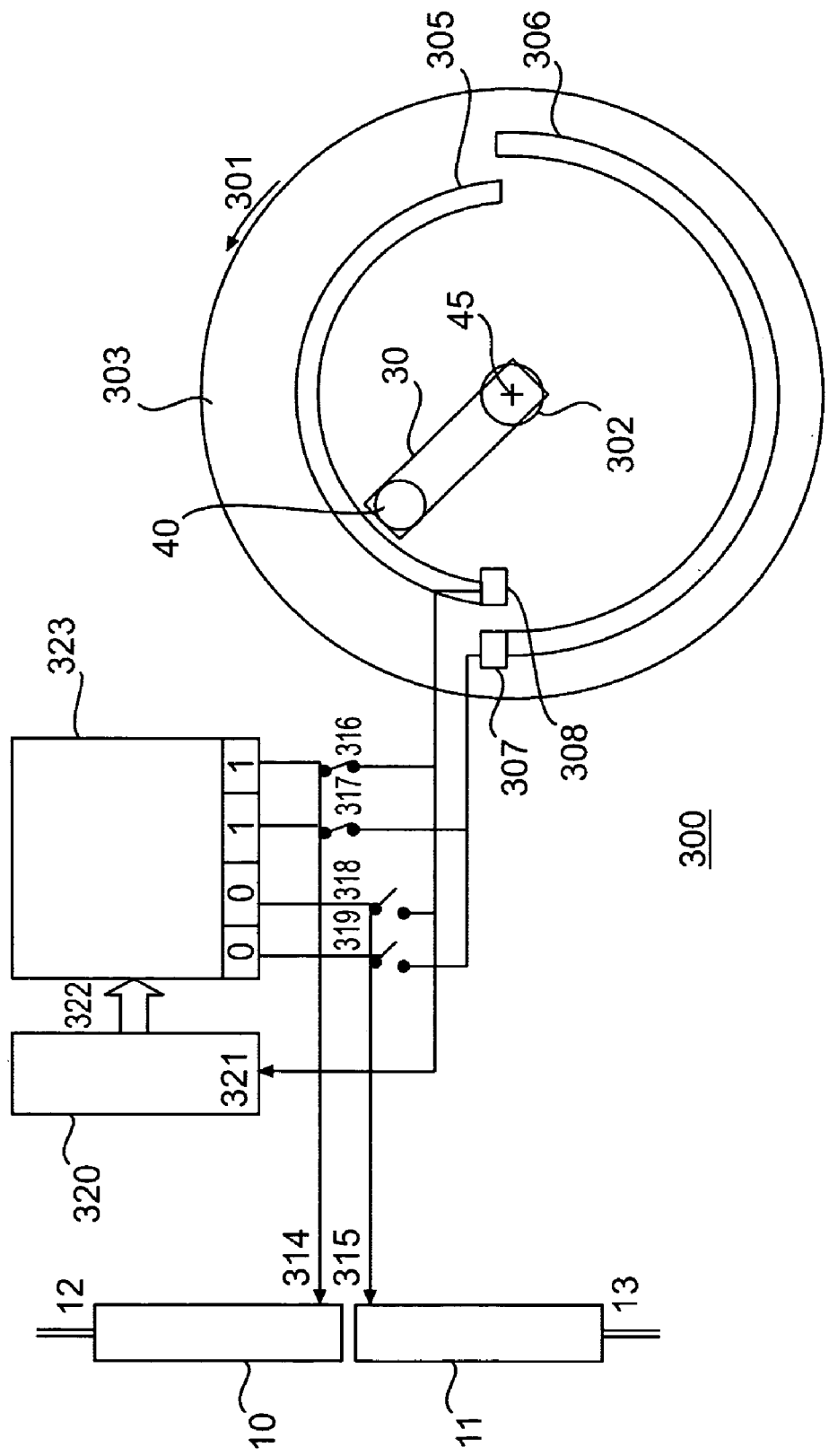
FIG. 16 is a schematic diagram of a control circuit for use in sensing apparatuses consistent with embodiments of the invention.

FIG. 16 illustrates a control circuit 300, which may be used instead of chopper 120 in any embodiment of the present invention requiring a chopper. Control circuit 300 provides allows apparatuses 601, 602 to selectively activate optical sources 10, 11 in response to the rotation of optical assembly 30 through leading arc 201 and trailing arc 202.

Control Circuit 300 utilizes electronic control input 314 to selectively activate optical source 10 and electronic control input 315 to selectively activate optical source 11. Electronic control inputs 314, 315 allow control circuit 300 to independently set the on or off state of optical sources 10, 11 by respectively setting the control inputs 314, 315 to on or off.

A plate 303 rotates in synchronization with optical assembly 30, in direction 301. Preferably, plate 303 is mounted on optical rotating assembly 30, with axis 45 passing through a central hole 302 on plate 303. Excitation light 12, 13 passes through hole 302 before entering optical assembly 30. As shown in FIG. 16, optical assembly 30 preferably is fixed at an angle after the beginning of opening 305, the angle coverage of opening 305 being larger than the sensing arc across the width of sample 90.

Plate 303 has an opening 305, which allows an optical fork sensor 308 to sense when optical assembly 30 passes through leading arc 201. Optical fork sensor 308 remains stationary while plate 303 and optical assembly 30 rotate. Optical fork sensor 308 outputs a sense signal of "one" during leading arc 201, when it senses light passing from its dedicated light source through cutout 305.

Digitizer disk 303 further also has a second opening 306, which allows a second optical fork sensor 307 to sense when optical assembly 30 passes through trailing arc 202. Optical fork sensor 307 remains stationary as plate 303 and optical assembly 30 rotate, sensing light passing from its dedicated light source through cutout 306. Optical fork sensor 307 outputs a sense signal of "one" during trailing arc 202.

As mentioned above, control circuit 300 is configured such that optical fork sensor 308 outputs a "one" sense signal during leading arc 201. Thus, for example, if switch circuit 316 is closed during leading arc 201, the sense signal from optical fork sensor 308 will travel to control input 314, causing optical source 10 to output excitation light 12.

The status of switch circuits 316, 317, 318 and 319 is controlled by 4 bits of the addressed output location of memory 323. A "one" sets the corresponding switch circuit on, and a "zero" turns it off. Thus, the addressed output location of memory 323 indicates whether the activation of optical sources 10, 11 is desired. A sequencer 320 controls the location in memory 323 that is read out to the switch circuits, through address bus 322. Sequencer 320 receives signals from optical fork sensor 308 via control input 321. When optical fork sensor 308 transitions from a sense signal of "zero" to a sense signal of "one," sequencer 320 increments the memory addresses in memory 323, changing the 4 output bits from memory 323 to the next 4 bits in a prestored sequence. In this manner, the memory address is incremented once per revolution of optical assembly 30, at the start of leading arc 201.

Switch circuits 316, 317, 318 and 319 control whether optical sources 10,11 receive signals from optical fork sensors 307, 308. Thus, control circuit 300 controls which of excitation light 12,13 illuminates sample 90 during leading arc 201 and trailing arc 202. Accordingly, control circuit 300 turns optical sources 10,11 on and off to selectively supply excitation light 12, 13 to sample 90.

Memory 323, sequencer 320, and address bus 322 have at least the capacity to store and output in sequence one 4-bit word for each of the revolution of the plate 303 required to conduct and complete the sensing of sample 90. A sequence of 4-bit output words from memory 323 can, for example, include all words having identical content, which would keep one or both optical sources 10, 11 on or off during the complete scanning operation. Also, it is possible that each 4-bit word in the sequence differs from the preceding 4-bit word, thereby allowing one or both of optical source 10 and optical source 11 to be switched on or off at each revolution during the complete scanning operation.

Optical sources 10,11 are thus independently controlled by the content of memory 323 via the electronic control inputs 314 and 315 during both leading arc 201 and trailing arc 202. Electronic chopper 300 may be configured to allow excitation light 12, 13 to reach sample 90 during leading arc 201, trailing arc 202, both arcs, or neither arc. Combinations of excitation light 12,13 during the leading arc 201 and trailing arc 202 provide for the various operational modes described above.

Figure 5:
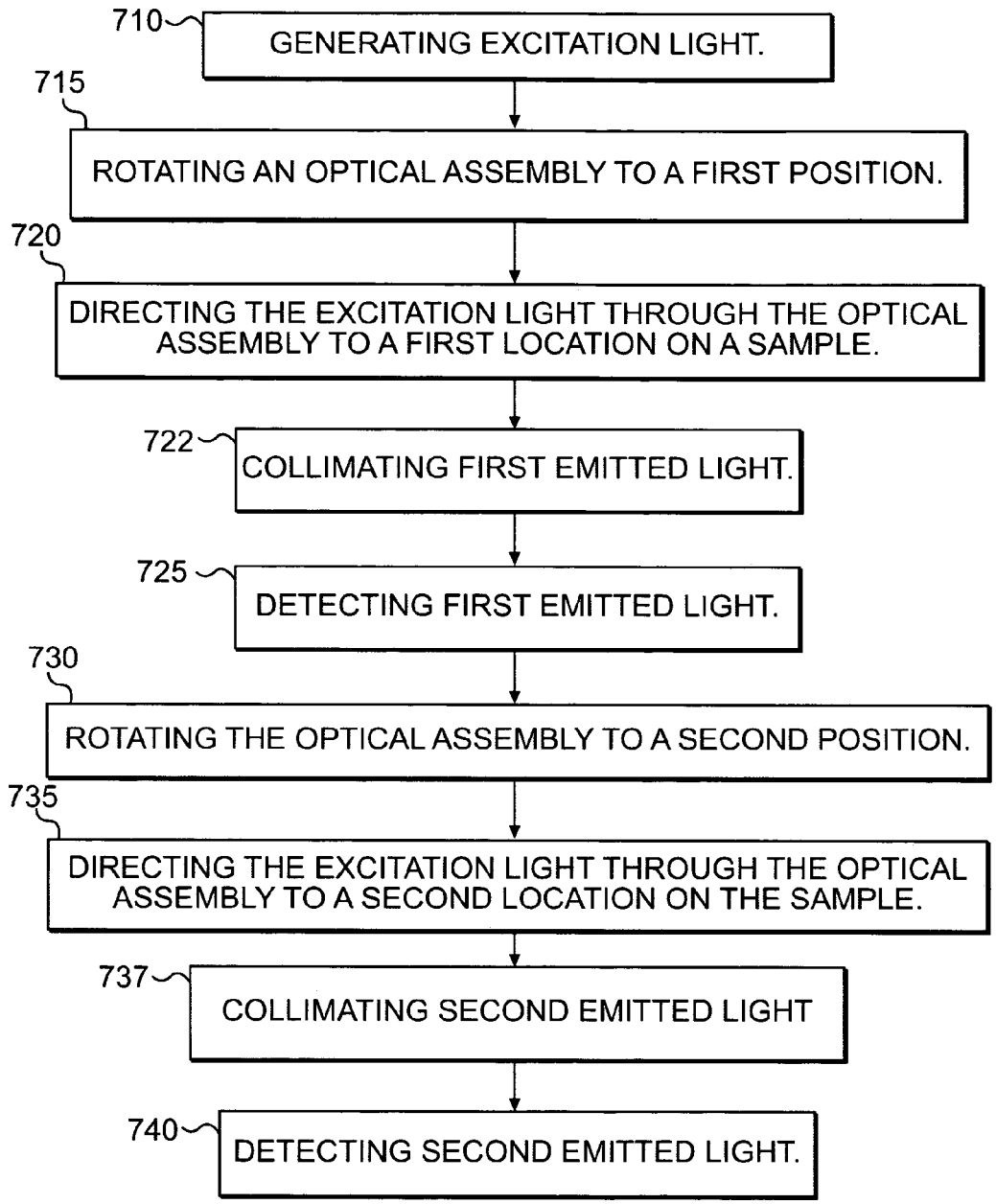
FIG. 5 is a flowchart of a sensing method consistent with another embodiment of the invention.

FIG. 5 illustrates a flow chart of a sensing method 700, consistent with a further aspect of the present invention.

In Step 710, excitation light is generated, preferably, where the wavelength is selected to cause a particular material in a sample to fluoresce, as noted above.

In Step 715, the optical assembly is rotated to a first position. Preferably, step 715 includes rotating the optical assembly about an axis. Moreover, it is preferable that the optical assembly is constructed in manner consistent with optical assembly 30, described above.

Next, in step 720, the excitation light is directed through the optical assembly to a first location on the sample. Preferably, the excitation light enters the optical assembly along the axis about which the optical assembly is rotated in step 715 and leaves the optical assembly along a second, substantially parallel axis. The excitation light may, however, enter the optical assembly along a different axis. The excitation light is preferable focused before reaching the sample.

It is desirable for the sample to include a biochip or other sample containing multiple testing sites.

In step 722, first emitted light—emitted by the sample—is received by a lens within the optical assembly and collimated into a first substantially parallel beam. This step is preferably performed using an aspherical lens provided in the optical assembly.

Preferably, between step 722 and 725, sensing method 700 further includes and directing the first beam toward a detecting device before detecting the first beam, which contains first emitted light. Moreover, consistent with the apparatuses described above, sensing method 700 may include filtering the first beam just before step 725.

In step 725, the first beam is detected. The first location on the sample fluoresces and emits the first emitted light, which is formed into the first beam, in response to the excitation light. Upon detecting the first beam, the method may include converting the first beam into an electric signal and storing or further processing that electric signal.

Next, in step 730, the optical assembly is rotated to a second position. Step 730 preferably includes rotating the optical assembly about the axis mentioned in conjunction with step 715 above.

In step 735, the excitation light is directed through the optical assembly to a second location on the sample. This step differs from step 720 in that the optical assembly now is in the second position, instead of the first position, causing the excitation light to be directed to the second location on the sample, instead of the first location on the sample.

In step 737, second emitted light is collimated into a second beam, preferably by a lens included within the optical assembly.

Between steps 737 and 740, sensing method 700 may further include directing the second beam toward a detecting device and filtering the second beam.

Finally, in step 740 the second beam is detected. As in step 725, step 740 may include converting the first beam into an electric signal and storing or further processing that electric signal.

Method 700 may further comprise moving the sample. Preferably, the moving step includes moving the sample in a linear direction substantially perpendicular to the axis about which the optical assembly is rotated. The moving step is preferably performed in a step-wise manner. A continuous, non-linear moving step may also be incorporated into method 700.

Method 700 may further include the utilization of one of the operational modes described above. For example, the first location specified in step 715 may be located on a first arc and the second location specified in step 730 may be located on a second arc. The first arc and second arc may be located on substantially opposite sides of a circle defined by the rotation of the optical assembly, the first and second arcs each spanning a width of the sample substantially perpendicular to a linear direction in which the sample moves. Selectively allowing excitation light to illuminate the sample in one or both steps 720 and 735 allows one to practice the single-channel modes of operation described above.

For example, the normal single-channel mode described in FIG. 11, would require that excitation light reach the sample only in step 720. Steps 730, 735, 737, and 740 would be eliminated, and the method would include rotating the optical assembly to a second location on the arc and directing the excitation light to the second location on that arc.

As another example, to practice the fast single-channel mode, where excitation light 12 reaches sample 90 during both the leading arc 201 and trailing arc 202, one would only need to modify method 700 to include the first and second arc described above.

Other adjustments necessary to practice each of the single-channel modes will be apparent from the description of FIGS. 11-14 above.

Figure 6:
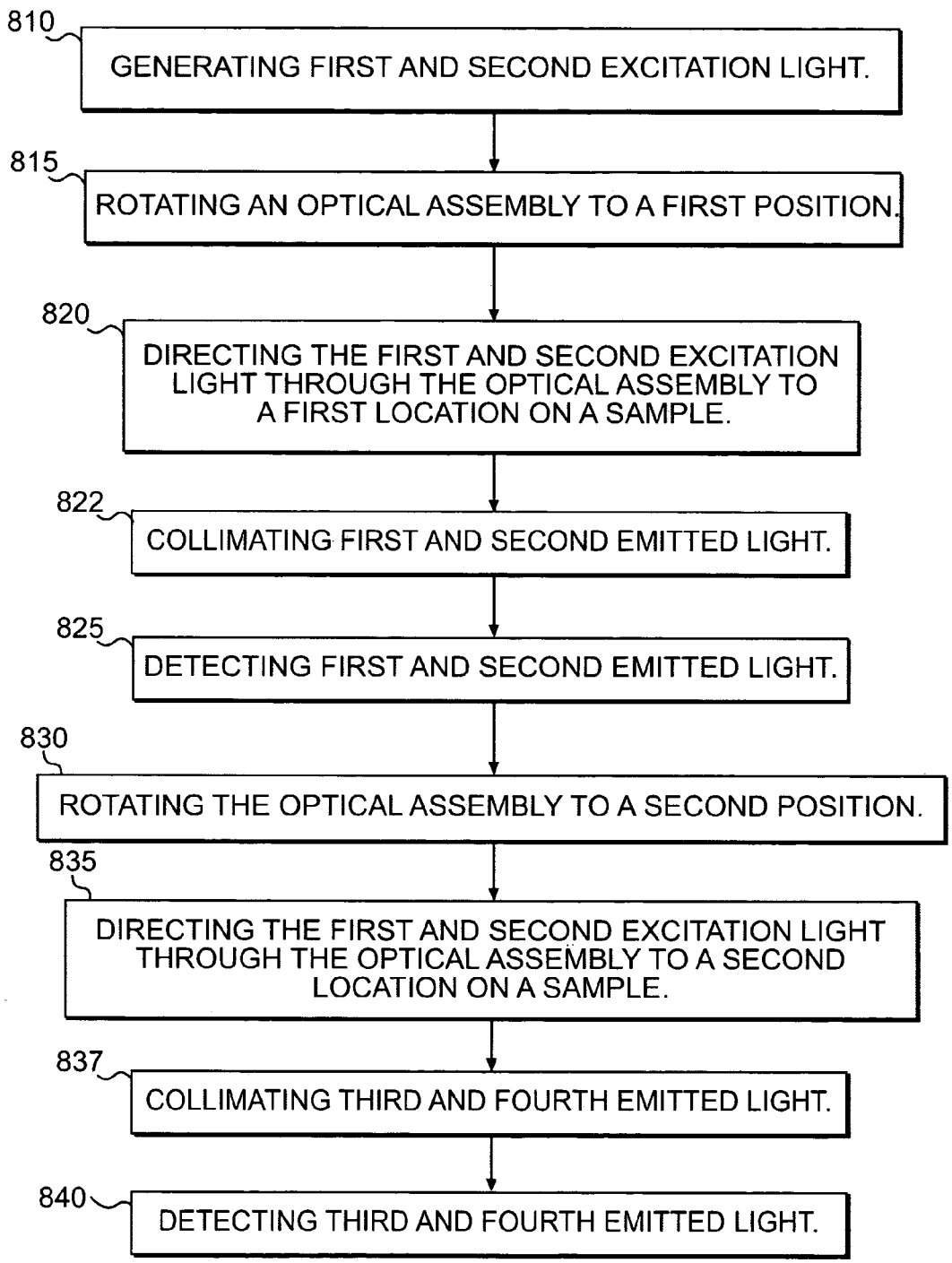
FIG. 6 is a flowchart of a sensing method consistent with an additional embodiment of the invention.

FIG. 6 illustrates sensing method 800, another sensing method consistent with the present invention.

In step 810, first and second excitation light are generated. Preferably, this step includes using a first laser to generate first excitation light and a second laser to generate second excitation light. The wavelengths of the first and second excitation light preferably differ, each being selected to cause a particular material to fluoresce.

In step 815, an optical assembly is rotated to a first position. Preferably, step 815 includes rotating the optical assembly about an axis. The optical assembly preferably is constructed in a manner consistent with optical assembly 30, described above.

In step 820, the first and second excitation light is directed through the optical assembly to a first location on a sample. This step is substantially similar to step 720 of method 700, except that step 820 includes directing two excitation lights, instead of a single excitation light. As in method 700, it is desirable for the sample to include a biochip or other sample containing multiple testing sites. Step 820 may further comprise directing one of the first excitation light and the second excitation light to the sample at a time.

Step 822 comprises collimating first and second emitted light, preferably by using a lens provided in the optical assembly. The first and second emitted light is collimated into first and second beams. Preferably, the photons of emitted light making up these first and second beams travel substantially parallel to one another. The first and second beam may overlap.

Preferably, the optical assembly directs the first and second emitted light toward one or more detecting devices before detecting the emitted light. Moreover, sensing method 800 may include filtering the first and second beams just before step 825.

In step 825, the first and second beams are detected. The first location on the sample emits first emitted light, which makes up the first beam, in response to the first excitation light and emits second emitted light, which makes up the second beam, in response to the second excitation light. Method 800 may further comprise converting the first and second emitted beam into an electric signal or signals and storing or further processing that electric signal or signals. Preferably, and consistent with sensing apparatus 602, described above, the first emitted light is detected with a different detector than the second emitted light. If first and second overlap, sensing method 800 may further include separating the first and second beams from one another before detection.

Next, in step 830, the optical assembly is rotated to a second position. Step 830 preferably includes rotating the optical assembly about the axis mentioned in conjunction with step 815 above.

In step 835, the first and second excitation lights are directed through the optical assembly to a second location on the sample. This step differs from step 820 in that the optical assembly now is in the second position, instead of the first position, causing the first and second excitation light to be directed to the second location on the sample, instead of the first location on the sample. Step 835 may further comprise directing one of the first excitation light and the second excitation light to the sample at a time.

In step 837, third and fourth emitted light—emitted by the sample from the second location—are collimated into third and fourth beams. The third and fourth beams may also be directed toward one or more detecting devices before detection. Moreover, sensing method 800 may include filtering the third and fourth beams and/or separating the third and fourth beams from one another.

Finally, step 840 comprises detecting the third and fourth beams. As in step 825, step 840 may include converting the third and fourth beams into an electric signal and storing or further processing that electric signal.

Method 800 may further comprise moving the sample. Preferably, the moving step includes moving the sample in a linear direction substantially parallel to the axis about which the optical assembly is rotated. The moving step is preferably performed in a step-wise manner. A continuous, non-linear moving step may also be incorporated into method 800.

Method 800 may further include the utilization of one of the operational modes described above. For example, the first location specified in step 815 and the second location specified in step 830 may be located on a first arc and a second arc, respectively. The first arc and second arc may be located on substantially opposite sides of a circle defined by the rotation of the optical assembly, spanning a width of the sample substantially perpendicular to a linear direction in which the sample moves. Selectively allowing first and second excitation light to illuminate the sample in each of steps 820 and 835 allows one to practice the dual-channel modes of operation described above.

For example, to practice the simultaneous dual-channel operational mode, where first and second excitation light are directed to the sample on both leading arc 201 and trailing arc 202 (See FIG. 12), method 800 need only be amended to include the arcs discussed above.

To practice the overlaid dual-channel mode illustrated in FIG. 15, for example, one would amend method 800 to direct only first excitation light to the sample in step 820 and direct only second excitation light to the sample in step 835. Moreover, step 825 would be amended to include detecting only the first beam, containing first emitted light, and step 840 would be amended to include only detecting the second beam, containing second emitted light emitted in response to second excitation light.

Other adjustments necessary to practice each of the dual-channel modes will be apparent from the descriptions of FIGS. 11-15 above.

The apparatuses and sensing methods described above allow users to quickly direct and receive light from distinct locations on samples. The apparatuses and sensing methods detect light emitted by samples containing multiple test sites arranged in a non-rectilinear patterns and can detect emitted light without moving the samples in rectilinear pattern. Moreover, samples used with the apparatuses and sensing methods described can comprise non-rectangular test sites.

It will be apparent to those skilled in the art that various modifications and variations can be made in the present invention without departing from the scope or spirit of the invention. As an example, excitation light 12 (and excitation light 13) may enter optical assembly 30 along an axis different than axis 45. Moreover, for example, additional optical sources, each producing laser beams having unique wavelengths, could be added to the sensing apparatus, enabling it measure more than two experimental results.

Some configurations consistent with the invention, moreover, may not include all of the components described above. For example, certain components, such as optical filters 60 and 62, may be omitted with little degradation of sensing capability in certain applications. While the sensing methods and apparatuses described herein include rotating optical assemblies 30, it is contemplated that the benefits of collimating emitted light 50, 61 may exist without the rotation of the optical assembly 30.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A sensing apparatus comprising:
a sample holder configured to receive a sample;
an optical source configured to emit excitation light;
an optical assembly configured to receive the excitation light, the optical assembly being spaced from the sample holder and being rotatable about a first axis;
an objective lens; and
a detector, wherein
the optical assembly is configured to direct the excitation light to a first location on the sample when the optical assembly is in a first position, and to direct the excitation light from the optical source to a second location on the sample when the optical assembly is rotated to a second position,
the optical assembly directs the excitation light to the sample along a second axis,
the objective lens is configured to collimate light emitted from the first and the second locations on the sample,
the detector is configured to receive the collimated light, and
a distance from the first axis to the second axis defines a radius of a circle, the circle comprises a first arc and a second arc, and the sensing apparatus is configurable to direct excitation light to the sample while the optical assembly rotates through the first arc and the second arc.

2. The sensing apparatus of claim 1, wherein the sensing apparatus directs excitation light to the sample while the optical assembly rotates through the first and second arcs.

3. The sensing apparatus of claim 1, wherein the optical source is a first optical source, the excitation light is first excitation light, the sensing apparatus further comprising a second optical source outputting second excitation light, wherein the sensing apparatus is configurable to direct second excitation light to the sample.

4. The sensing apparatus of claim 3, wherein the sensing apparatus directs first excitation light to the sample while the optical assembly rotates through the first arc, and the sensing apparatus directs second excitation light to the sample while the optical assembly rotates through the second arc.

5. The sensing apparatus of claim 3, wherein the sensing apparatus directs first and second excitation light to the sample while the optical assembly rotates through the first arc, and the optical source directs first and second excitation light to the sample while the optical assembly rotates through the second arc.

6. The sensing apparatus of claim 3, wherein the sensing apparatus directs first excitation light to the sample while the optical assembly completes a first rotation around the circle, and the sensing apparatus directs second excitation light to the sample while the optical assembly completes a second rotation around the circle.

7. The sensing apparatus of claim 3, further comprising an optical chopper configured to allow one of the first excitation light and the second excitation light to reach the sample at a time.

8. The sensing apparatus of claim 3, further comprising a second detector, wherein the first detector is configured to detect first light emitted by the sample in response to the first excitation light and the second detector is configured to detect second light emitted by the sample in response to the second excitation light.

9. The sensing apparatus of claim 1, wherein the optical assembly comprises a mirror, the mirror being aligned with the second axis, and the mirror reflecting the excitation light.

10. The sensing apparatus of claim 1, wherein the objective lens comprises an aspherical lens.

11. The sensing apparatus of claim 1, wherein the detector is aligned along the first axis.

12. The sensing apparatus of claim 1, wherein the sample includes a biochip.

13. The sensing apparatus of claim 1, wherein the sample holder is configured to move.

14. The sensing apparatus of claim 13, wherein the sample holder is configured to move in a linear direction.

15. The sensing apparatus of claim 1, wherein the detector comprises a photomultiplier tube.

16. The sensing apparatus of claim 15, wherein the objective lens collimates the emitted light into a beam that substantially covers a light-sensing surface of the photomultiplier tube.

17. The sensing apparatus of claim 1, wherein the optical source comprises a laser.

* * * * *